United States Patent [19]
Gerecke et al.

[11] 3,954,764
[45] May 4, 1976

[54] DIBENZO [b,f]THIEPINS BEARING PIPERAZINYL SUBSTITUTION

[75] Inventors: Max Gerecke, Reinach; Jean-Pierre Kaplan, Le Plessis Robinson; Emilio Kyburz, Reinach, all of Switzerland

[73] Assignee: Hoffmann-la Roche Inc., Nutley, N.J.

[22] Filed: May 17, 1974

[21] Appl. No.: 471,094

Related U.S. Application Data

[63] Continuation-in-part of Ser. No. 378,732, July 12, 1973, abandoned.

[30] Foreign Application Priority Data

Mar. 30, 1973 Switzerland.......................... 4605/73
Jan. 14, 1974 Switzerland............................ 448/74

[52] U.S. Cl.............................. 260/268 TR; 424/250
[51] Int. Cl.². ...................................... C07D 295/12
[58] Field of Search............................. 260/268 TR Primary Examiner—Joseph A. Narcavage
Assistant Examiner—Jose Tovar
Attorney, Agent, or Firm—Samuel L. Welt; George M. Gould; William G. Isgro

[57] ABSTRACT

Compounds of the formulas

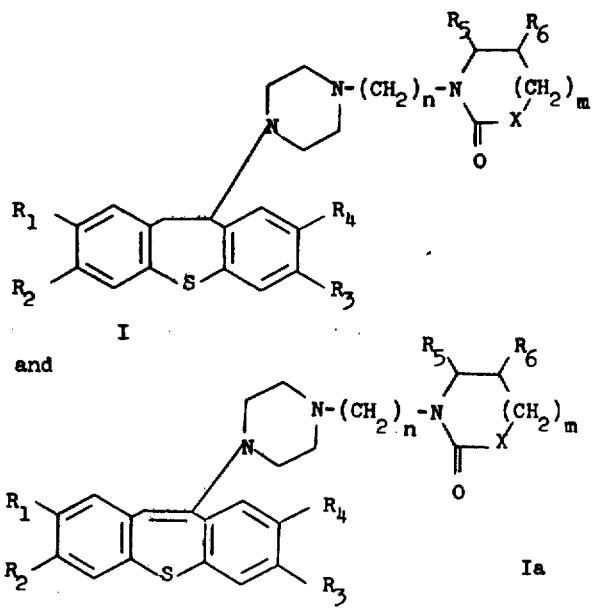

wherein $R_1$, $R_2$, $R_3$, $R_4$, $R_5$, $R_6$, $m$ and $n$ and X are as hereinafter set forth, are described. The compounds of formulas I and Ia are useful as neuroleptic agents.

15 Claims, No Drawings

DIBENZO [B,F]THIEPINS BEARING PIPERAZINYL SUBSTITUTION

CROSS-REFERENCE TO RELATED APPLICATIONS

This application is a continuation-in-part application of U.S. Pat. application Ser. No. 378,732, filed July 12, 1973, now abandoned.

BRIEF SUMMARY OF THE INVENTION

The invention relates to compounds of the formulas

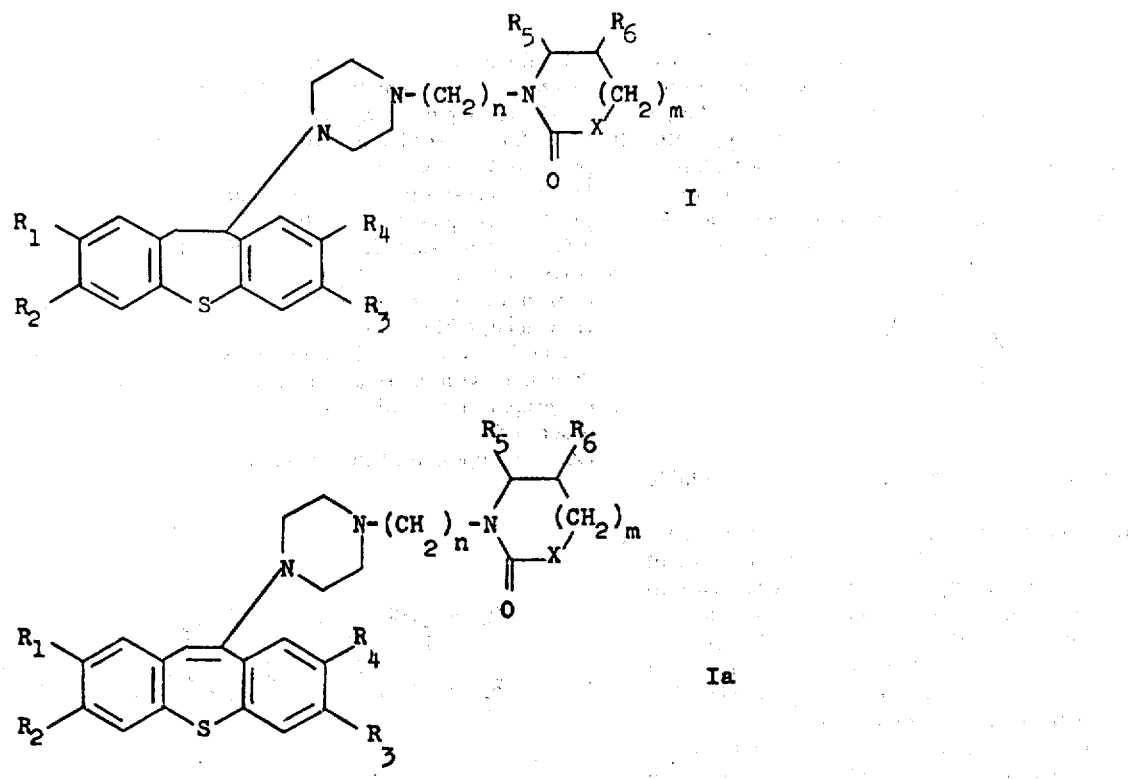

wherein one of $R_1$ and $R_2$ or, respectively, $R_3$ and $R_4$ is hydrogen and the other is methyl, methoxy, methylthio, dimethylsulfamoyl, chloro, fluoro or trifluoromethyl, $n$ is 2 or 3; $m$ is 0 or 1; X is sulfur, oxygen, imino, lower alkylimino or methylene, and $R_5$ and $R_6$ are hydrogen or together are the group

and salts thereof with pharmaceutically acceptable acids.

DETAILED DESCRIPTION OF THE INVENTION

The invention relates to compounds of the formulas

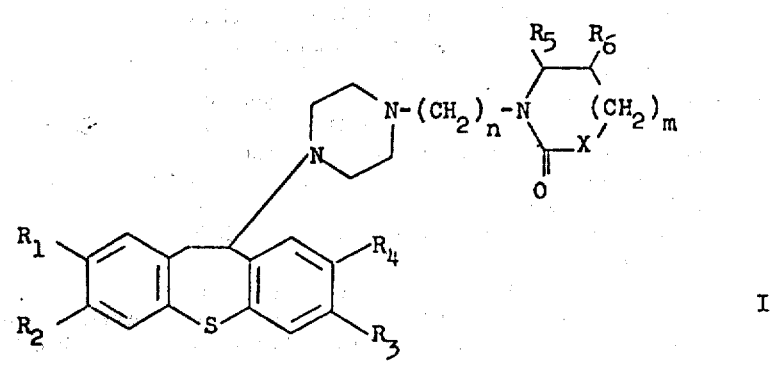

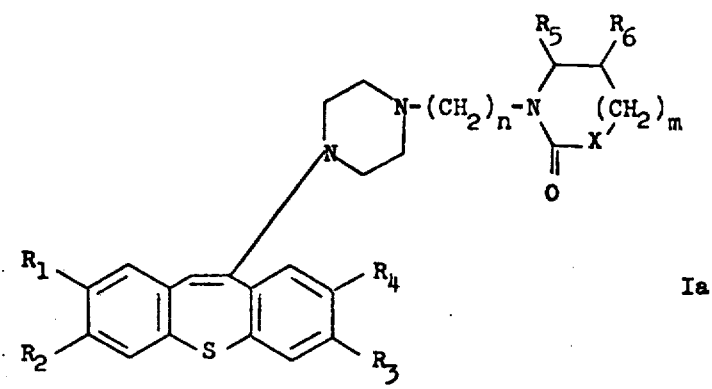

Ia wherein one of $R_1$ and $R_2$ is hydrogen and the other is methyl, methoxy, methylthio, dimethylsulfamoyl, chloro, fluoro or trifluoromethyl; one of $R_3$ and $R_4$ is hydrogen and the other is methyl, methoxy, methylthio, dimethylsulfamoyl, chloro, fluoro or trifluoromethyl; $n$ is 2 or 3; $m$ is 0 or 1; X is sulfur, oxygen, imino, lower alkylimino or methylene; and $R_5$ and $R_6$ are hydrogen or taken together are the group

and salts thereof with pharmaceutically acceptable acids.

According to the above-specified definition, the benzyl [b,f]thiepin of formulas I and Ia bears a substituent in each of the aromatic rings. One substituent is carried in the 2- or 3-position, and the other in the 7- or 8-position of the dibenzo[b,f]thiepin molecule. It has been found that the compounds of formulas I and Ia of the invention and their pharmaceutically acceptable addition salts which are new compounds, demonstrate a strong central depressant effect and neuroleptic activity. They can, therefore, for example, be utilized in the treatment of acute or chronic schizophrenia as well as tranquilizers. Of particular advantage is the fact that the compounds of the invention demonstrate a lack of or only weak cataleptic side effects so that no or insignificant motor disturbances are observed.

Preferred compounds of the invention are those of formula I, as well as their salts with pharmaceutically acceptable acids. Preferred compounds of formulas I and Ia are those wherein $R_2$ and $R_3$ are hydrogen, $R_1$ is methyl and $R_4$ is chloro, fluoro or methylthio, as well as their pharmaceutically acceptable acid addition salts.

Another preferred group of compounds of formulas I and Ia comprises one wherein $R_2$ and $R_3$ are hydrogen $R_1$ is chloro and $R_4$ is fluoro, as well as their salts with parmaceutically acceptable acids. pharmaceutically Yet another preferred group of compounds of formulas I and Ia comprises one wherein $R_1$ and $R_3$ are hydrogen; $R_2$ is methoxy and $R_4$ is methylthio, as well as their salts with pharmaceutically acceptable acids.

Still another preferred group of compounds of formulas I and Ia comprises one wherein $n$ is 2; $m$ is 0; X is oxygen or methylene and $R_5$ and $R_6$ are hydrogen, as well as their salts with pharmaceutically acceptable acids.

Preferred compounds of the invention are 1-{2-[4-(8-chloro-10,11-dihydro-2-methyl-dibenzo[b,f]thiepin-10-yl)-1-piperazinyl]ethyl}-2-pyrrolidinone, 3-{2-[4-(8-fluoro-10,11-dihydro-2-methyldibenzo[b,f]thiepin-10-yl)-1-piperazinyl]-ethyl}-2-oxazolidinone, 3-{2-[4-(2-chloro-8-fluoro-10,11-dihydro-dibenzo[b,f]thiepin-10-yl)-1-piperazinyl]-ethyl}-2-oxazolidinone and 3-{2-[4-(10,11-dihydro-2-methyl-8methylthio-dibenzo[b,f]thiepin-10-yl)-1-piperazinyl]-ethyl}-2-oxazolidinone, as well as their salts with pharmaceutically acceptable acids.

The 10,11-saturated compounds of formula I and their salts with pharmaceutically acceptable acids cam be prepared according to the processes hereinafter described:

(A) A compound of the formula

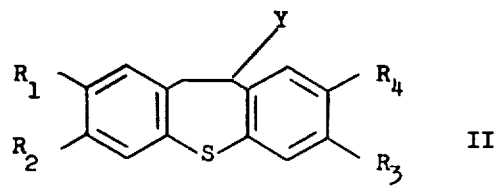

II wherein $R_1$, $R_2$, $R_3$ and $R_4$ are as hereinbefore described, and Y is a leaving group, is reacted with a compound of the formula

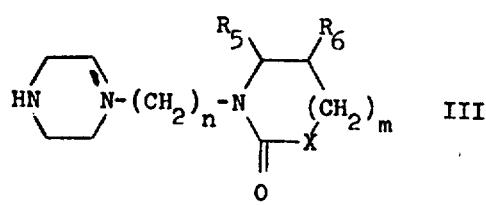

III wherein $n$, $m$, X, $R_5$ and $R_6$ are as hereinbefore described or (B) A compound of the formula

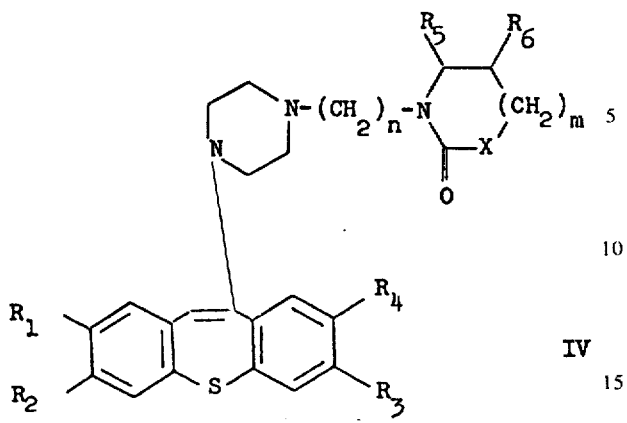

wherein $R_1$, $R_2$, $R_3$ and $R_4$, $n$, $m$, $X$, $R_5$ and $R_6$ are as hereinbefore described,
is reduced, or
(C) A compound of the formula

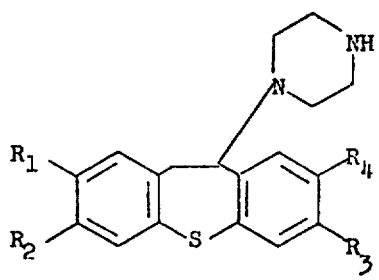

wherein $R_1$, $R_2$, $R_3$ and $R_4$ are as hereinbefore described,
is reacted with a compound of the formula

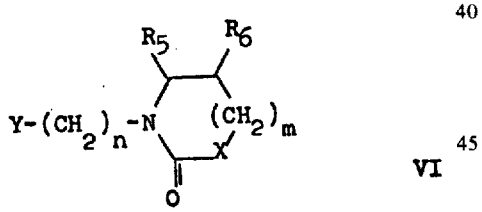

wherein Y, $n$, $m$, X, $R_5$ and $R_6$ are as hereinbefore described,
and, if desired, the resulting products can be converted to their pharmaceutically acceptable acid addition salts.

The 10,11-unsaturated compounds of formula Ia and their pharmaceutically acceptable acid addition salts can be prepared in accordance with the invention by a process which is hereinafter described, that is, a compound of the formula

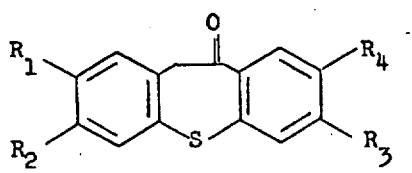

wherein $R_1$, $R_2$, $R_3$ and $R_4$ are as hereinbefore described,
is reacted with a compound of the formula

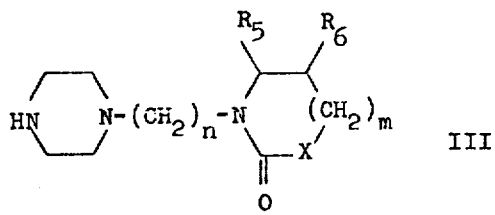

wherein $n$, $m$, X, $R_5$ and R6 are as hereinbefore described,
and, if desired, the resulting product is then converted to a pharmaceutically acceptable acid addition salt.

The leaving group Y in the starting material of formula II is preferably halogen or alkyl-substituted or aryl-substituted sulfonyloxy. Preferably, the alkyl group of the sulfonyloxy substituent is lower alkyl, such as methyl and preferably the aryl group of the sulfonyloxy substituent is phenyl or p-tolyl. The halogen substituent is preferably chlorine or bromine.

The Y group of the starting material of formula II can, for example, be introduced in the following manner:

When Y is to be halogen, the corresponding 10-hydroxy compound is reacted with an appropriate halogenating agent, for example, thionyl chloride, thionyl bromide, or with a hydrogen halide in the presence of a dehydrating agent, for example hydrogen chloride and calcium chloride.

When Y is to be alkyl-substituted or aryl-substituted sulfonyloxy, the corresponding 10-hydroxy compound is reacted with an alkyl-substituted or arylsubstituted sulfonic acid halide, for example, the chloride.

The starting materials of formula III can, for example, be prepared by the following reaction:

A compound of the formula

wherein $R_7$ is a protecting group, for example, benzyl or a lower alkoxycarbonyl group, for example, methoxycarbonyl, ethoxycarbonyl or the like,
is condensed with a compound of the formula

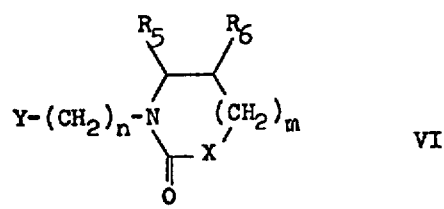

wherein Y, $n$, $m$, $R_5$, $R_6$ and X are as hereinbefore described,
in the presence of an acid-binding agent such as potassium carbonate or triethylamine. The reaction product of the formula

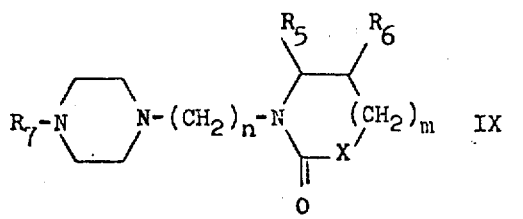

wherein $R_5$, $R_6$, $R_7$, $n$, $m$ and X are as hereinbefore described,
is subsequently treated to remove the protecting group which in the case of the benzyl group is removed by hydrogenolysis and in the case of the alkoxycarbonyl group, is removed by hydrolyis, for example, with an aqueous alkali, to yield the compound of formula III.

The reaction of the starting materials of formulas II and III in accordance with the process of the invention can be carried out without the addition of a solvent. However, if a solvent is utilized, preferably it is an organic solvent, for example, an aromatic hydrocarbon such as benzene or toluene, a lower alkanol such as methanol or ethanol, a chlorinated hydrocarbon such as methylene chloride, trichloroethylene, chloroform, carbon tetrachloride or chlorobenzene, an aliphatic or cyclic ether such as diethyl ether, tetrahydrofuran or dioxane, or dimethylformamide or dimethylsulfoxide. The temperature at which the reaction is carried out, preferably is in the range of from about 30° to about 200°; the most preferred temperature is in the range of about 60° to about 150°. Advantageously, the reaction is carried out in the presence of an acid-binding agent, for example, in the presence of an alkali carbonate such as potassium carbonate or it is carried out in the presence of an excess of the starting material of formula III.

The starting enamines of formula IV are likewise end products of formula Ia. The enamines of formula IV are prepared in accordance with the invention by reaction the corresponding 10-oxo compound of formula VII with a compound of formula III. For example, the reaction is carried out in the presence of a strong acid in an aromatic solvent at a temperature, for example, in the range of from about 80° to about 150°. As the acid there can be utilized, for example, mineral acids such as sulfuric acid or hydrochloric acid, or a strong organic acid such as methanesulfonic acid or toluenesulfonic acid. As the aromatic solvent, preferably there is utilized benzene, toluene or o-, m-, or p-xylene. By heating, there is formed an azeotrope between the solvent and the water which is formed in the reaction, which can be distilled. The water which is formed can also be removed by the addition of a dehydrating agent such a titanium tetrachloride or the like.

The reduction of the enamines of formula IV in accordance with the invention, preferably is carried out by treatment with an alkali metal borohydride in the presence of a strong acid. As the alkali metal borohydride, preferably there can be used sodium or potassium borohydride, especially sodium borohydride. It is also possible to utilize lithium borohydride. The strong acid can either be an organic or an inorganic acid. As an organic acid, there can be utilized straight or branched chain lower mono- or dicarboxylic acids with up to 4 carbon atoms, which can be substituted by halogen, for example, formic acid, acetic acid, trichloroacetic acid, trifluoroacetic acid, propionic acid, isobutyric acid, oxalic acid and the like. Preferred is acetic acid; especially preferred is oxalic acid. As an inorganic acid, there can be utilized, for example, sulfuric acid, hydrochloric acid, especially hydrochloric acid, and the like. A preferred inorganic acid is concentrated sulfuric acid.

The enamine of formula IV is unstable in the presence of water. Therefore, the reduction suitably is carried out in the absence of water. The reaction is preferably carried out in an anhydrous acid or only in such acids where should they contain water, the water is not released, for example, concentrated sulfuric acid.

The reaction of the alkali metal borohydride and the strong acid can, advantageously, be carried out in the presence of an ether such as diethyl ether, tetrahydrofuran, dioxane, diethyleneglycol dimethyl ether (diglyme) or dimethoxyethane, at a temperature in the range of about room temperature and the reflux temperature of the solvent. Preferred is the reflux temperature.

The reduction of the enamine of formula IV can be carried out by other methods, for example, by the treatment with formic acid or with zinc and acetic acid. The foregoing reaction is preferably carried out at a temperature between about room temperature and the reflux temperature of the solvent; preferably at the reflux temperature.

The starting material of formula V can, for example, be prepared by reacting a compound of formula II with a mono-N-protected piperazine, for example, N-carbethoxy-piperazine. The condensation product is subsequently hydrolyzed, for example, with the aid of an aqueous alkali. Yet another method comprises the reaction of the above-mentioned mono-N-protected piperazine, for example, N-carbethoxy-piperazine, essentially in the same manner as that described for the reaction between the compounds of formulas VII and III. The so-obtained N-protected enamine can have its 10,11-double bond reduced in a similar manner to that described above for the reduction of the enamine of formula IV, and subsequently the protecting group can be hydrolyzed, for example, with the aid of an aqueous alkali.

The leaving group of the starting material of formula VI has the same meaning as in the case described for the starting material of formula II. The starting materials of formula VI can be prepared, for example, by treatment of a lactam alkali metal salt of the formula

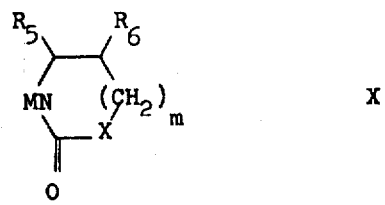

wherein $R_5$, $R_6$, $m$ and X are as previously described,
and M is an alkali metal, such as sodium or the like, with ethylene oxide or propylene oxide and by reacting the so-obtained N-hydroxy-ethyl or N-hydroxy-propyl compound, respectively, with a halogenating agent such as thionyl chloride or with an alkyl-substituted or aryl-substituted sulfonic acid halide, for example, the chloride.

Starting materials of formula VI wherein Y is a chlorine atom can also be prepared by reacting 1-bromo-2-chloroethane or 1-bromo-3-chloropropane with an alkali metal salt lactam of formula X.

The reaction of the starting materials of formulas V and VI in accordance with the invention, conveniently can be carried out in an inert organic solvent, for example, in an aromatic hydrocarbon such as benzene or toluene, a chlorinated hydrocarbon such as chloroform, an ether such as dioxane or dimethoxyethane, a lower alkanol such as methanol or ethanol, a ketone such as acetone or methylethyl ketone, or dimethylformamide or dimethylsulfoxide. It is preferred to carry out the above reaction in the presence of an acid-binding agent, for example, in the presence of an alkali metal carbonate, such as sodium or potassium carbonate, or in the presence of an inorganic base such as triethylamine. As the acid-binding agent, there can be utilized an excess of the base of formula V. The temperature at which the reaction is carried out preferably is in the range of about room temperature and the boiling point of the reaction mixture.

The starting materials of formula VII, as well as the corresponding 10-hydroxy compound referred to herein, are known compounds or can be prepared according to known procedures. The reaction of a compound of formula VII with a compound of formula III leads to a 10,11-unsaturated enamine of formula I. This reaction is carried out, for example, in the presence of a strong acidic agent in an aromatic solvent with heating, for instance, at a temperature in the range of from about 80° to about 150°C. Exemplary of the acidic agents which can be used are a mineral acid such as sulfuric acid or hydrochloric acid, a strong organic acid such as methanesulfonic acid or p-toluenesulfonic acid, or the like. As the aromatic solvent, there can be preferably used benzene, toluene or o-, m- or p-xylene. During the heating, an azeotrope is formed between the solvent and the water formed in the reaction. The azeotrope can be removed by distillation. The water which forms in the reaction can also be removed by adding a dehydrating agent such as, for example, titanium tetrachloride.

The bases of formulas I and Ia form salts with inorganic, as well as with organic acids, for example, they form salts with hydrohalic acids such as hydrochloric acid, hydrobromic acid or hydroiodic acid, with other mineral acids such as sulfuric acid, phosphoric acid, or nitric acid, as well as with organic acids such as acetic acid, citric acid, camphorsulfonic acid, methanesulfonic acid, toluenesulfonic acid, salicyclic acid, ascorbic acid, maleic acid, mandelic acid, or the like. Preferred salts are those formed with hydrohalic acids, especially preferred are those formed with hydrochloric acid and maleic acid. The acid addition salts can be prepared, preferably, in a solvent such as ethanol, acetone or acetonitrile, by treatment of the free base with the corresponding anhydrous acid. Depending on the molar ratio of free base to acid, there is obtained, because of the two nitrogen atoms in the piperazine moiety, a mono- or a di-salt with one or two moles of acid per mole of base, respectively. In the working up of a salt, there is obtained, depending on the solubility of the mono- or di-salt in the solvent used, the corresponding monoor di-salt.

The bases of formulas I and Ia are partly crystalline, solid substances, which are relatively soluble in dimethylsulfoxide, dimethylformamide or in chlorinated hydrocarbons such as chloroform, methylene chloride or in an alkanol such as methanol or ethanol and are relatively insoluble in water.

The pharmaceutically acceptable acid addition salts of the bases of formulas I and Ia are crystalline, solid substances, which are freely soluble in dimethylsulfoxide, dimethylformamide, or in an alkanol such as methanol or ethanol, and partially soluble in chloroform, methylene chloride or water. They are relatively insoluble in benzene, ether or petroleum ether.

The compounds of formulas I and Ia are useful as central depressants and neuroleptic agents, substantially devoid of cataleptic activity or effect.

A cataleptic effect ("wax-like rigidity", that is, maintaining for an abnormally long period a forced upon body position) is considered to be a disturbing side effect with central depressants and neuroleptically active compounds and indicates motor disturbances. The products according to the invention have the advantage that they do not have this disturbing side effect or have it only to a very slight extent. To prove the lack of cataleptic activity, representative samples of the end products of the invention were administered intraperitoneally to rats. The following compounds were tested:

Product A: 1-{2-[4-(8-chloro-10,11-dihydro-2-methyl-dibenzo[b,f]thiepin-10-yl)-1-piperazinyl]-ethyl}-2-pyrrolidinone maleate;

Product B: 3-{2-[4-(2-chloro-7-fluoro-10,11-dihydrodibenzo[b,f]thiepin-10-yl)-1-piperazinyl]-ethyl}-2-oxazolidinone maleate;

Product C: 3-{2-[4-(8-fluoro-10,11-dihydro-2-methyl-dibenzo[b,f]thiepin-10-yl)-1-piperazinyl]-ethyl}-2-oxazolidinone;

Product D: 3-{2-[4-(2-chloro-8-fluoro-10,11-dihydrodibenzo[b,f]thiepin-10-yl)-1-piperazinyl]-ethyl}-2-oxazolidinone maleate;

Product E: 3-{2-[4-(10,11-dihydro-2-methyl-8-methylthiodibenzo[b,f]thiepin-10-yl)-1-piperazinyl]-ethyl}-2-oxazolidinone maleate.

The foregoing compounds were compared to chlorpromazine, a well-known central depressant, especially well known as a neuroleptic agent.

The test animals are considered to be cataleptic when the homolateral extremities remain in the crossed position for at least 10 seconds. The number of cataleptic animals is recorded every 30 minutes over a 6-hour period. The $ED_{50}$ is the dose at which 50 percent of the animals are cataleptic.

| RESULTS Product | $ED_{50}$ mg/kg |
|---|---|
| 1-{2-[4-(8-chloro-10,11-dihydro-2-methyl-dibenzo[b,f]thiepin-10-yl)-1-piperazinyl]-ethyl}-2-pyrrolidinone maleate (Product A) | >100 |
| 3-{2-[4-(2-chloro-7-fluoro-10,11-dihydro-dibenzo[b,f]thiepin-10-yl)-1-piperazinyl]-ethyl}-2-oxazolidinone maleate (Product B) | >100 |
| 3-{2-[4-(8-fluoro-10,11-dihydro-2-methyl-dibenzo[b,f]thiepin-10-yl)-1-piperazinyl]-ethyl} 2-oxazolidinone (Product C) | 75 |
| 3-{2-[4-(2-chloro-8-fluoro-10,11-dihydro-dibenzo[b,f]thiepin-10-yl)-1-piperazinyl]-ethyl}-2-oxazolidinone maleate (Product D) | 45 |
| 3-{2-[4-(10,11-dihydro-2-methyl-8-methylthio-dibenzo[b,f]thiepin- | |

-continued

RESULTS

| Product | ED$_{50}$ mg/kg. |
|---|---|
| 10-yl)-1-piperazinyl]-ethyl}-2-oxazolidinone maleate (Product E) | 45 |
| Chlorpromazine | 6 |

The table demonstrates that there was no cataleptic effect produced by Products A and B of the invention, very weak cataleptic activity produced by Product C of the invention and considerably lower cataleptic activity produced by Products D and E of the invention, as compared to chlorpromazine, which does demonstrate cataleptic effect.

Furthermore, Products A to E are considerably less toxic than chlorpromazine as can be seen from the acute toxicity results, which are detailed hereinafter, obtained in the mouse. The toxicity results are based on the duration of action the compounds of formulas I and Ia over a period of 24 hours.

RESULTS

| Product | LD$_{50}$ mg/kg p.o. |
|---|---|
| 1-{2-[4-(8-chloro-10,11-dihydro-2-methyl-dibenzo[b,f]thiepin-10-yl)-1-piperazinyl]-ethyl}-2-pyrrolidinone maleate (Product A) | 3750 |
| 3-{2-[4-(2-chloro-7-fluoro-10,11-dihydro-dibenzo[b,f]thiepin-10-yl)-1-piperazinyl]-ethyl}-2-oxazolidinone maleate (Product B) | 900 |
| 3-{2-[4-(8-fluoro-10,11-dihydro-2-methyl-dibenzo[b,f]thiepin-10-yl)-1-piperazinyl]-ethyl}-2-oxazolidinone (Product C) | 1875 |
| 3-{2-[4-(2-chloro-8-fluoro-10,11-dihydro-dibenzo[b,f]thiepin-10-yl)-1-piperazinyl]-ethyl}-2-oxazolidinone maleate (Product D) | 450 |
| 3-{2-[4-(10,11-dihydro-2-methyl-8-methylthio-dibenzo[b,f]thiepin-10-yl)-1-piperazinyl]-ethyl}-2-oxazolidinone maleate (Product E) | 3750 |
| Chlorpromazine | 200 |

To demonstrate the central depressant effect, especially the neuroleptic effects of the products of the invention, representative compounds were utilized in the following tests:

I. Rotating Rod Test

In the Rotating Rod Test, the ability of mice to achieve a coordinated motor performance is investigated. After peroral administration of the test substance, the mice are placed upon a horizontal slowly rotating rod and the time they remain on the rod is recorded. The ED$_{50}$ is that dose which reduces the holding on period of the mice by 50 percent as compared to the holding on period prior to the administration of the test substance.

Products A, C and D in the test demonstrate a strong activity (Product A: ED$_{50}$ = 7.3 mg/kg; Product C: ED$_{50}$ = 2.1 mg/kg; Product D: ED$_{50}$ = 1.0 mg/kg), which for C and D is superior to that of chlorpromazine (ED$_{50}$ = 5 mg/kg) and for A approximates that of chlorpromazine.

II. Determination of Homovanillinic Acid

Two hours prior to being killed, rats are injected with the test substance.

Thereafter, the homovanillinic acid is extracted from the supernatant portion of a homogenized mixture of the brains of the treated rats into butyl acetate and later into an aqueous solution and is oxidized with potassium ferric cyanide to a fluorescent dimer. From an increased concentration of homovanillinic acid (HVA), it can be demonstrated that the test substance works the same as chlorpromazine, that is, it increases the turnover of dopamine in the basal ganglions. The homovanillinic acid titer in untreated rats is arbitrarily set at 100 percent.

RESULTS

| Product | Dose mg/kg p.o. | Increase in HVA, percent |
|---|---|---|
| 1-{2-[4-(8-chloro-10,11-dihydro-2-methyl-dibenzo[b,f]thiepin-10-yl)-1-piperazinyl]-ethyl}-2-pyrrolidinone maleate (Product A) | 50 | 295 |
| 3-{2-[4-(2-chloro-7-fluoro-10,11-dihydro-dibenzo[b,f]thiepin-10-yl)-1-piperazinyl]-ethyl}-2-oxazolidinone maleate (Product B) | 50 | 270 |
| 3-{2-[4-(8-fluoro-10,11-dihydro-2-methyl-dibenzo[b,f]thiepin-10-yl)-1-piperazinyl]-ethyl}-2-oxazolidinone maleate (Product C) | 50 | 235 |
| 3-{2-[4-(2-chloro-8-fluoro-10,11-dihydro-dibenzo[b,f]thiepin-10-yl)-1-piperazinyl]-ethyl}-2-oxazolidinone maleate (Product D) | 45 | 300 |
| 3-{2-[4-(10,11-dihydro-2-methyl-8-methylthio-dibenzo[b,f]thiepin-10-yl)-1-piperazinyl]-ethyl}-2-oxazolidinone maleate (Product E) | 50 | 255 |
| Chlorpromazine | 20 | 321 |

In this test, Products A, B and D demonstrate an activity which is nearly as potent as that of chlorpromazine.

III. "Pole Climbing" Test

This test provides information about behavioral reactions of rats. Rats are trained to avoid, by climbing up a vertical pole in the test chamber, an electrical impulse (unconditioned impulse) released via the wire-latticed floor some seconds after an acoustic signal (conditioned impulse).

The blocking of the conditioned reaction is determined by the parameter ED$_{50}$ (mg/kg p.o.); the blocking of the unconditioned reaction is determined by a parameter ED$_{10}$ (mg/kg. p.o.).

The parameter ED$_{50}$ (blocking of the conditioned reaction) gives a measure of the neuroleptic strength of action of the test substance. The quotient ED$_{10}$ (blocking of the unconditioned reaction)/ED$_{50}$ (blocking of the conditioned reaction) gives a measure of the quality of action of the test substance since, with increasing quotient, a greater selectivity of the neuroleptic action (slighter neurotoxic side-effect) is present.

| Product | RESULTS ED$_{50}$ (blocking of the conditioned reaction) mg/kg. p.o. | Quotient ED$_{10}$ (blocking of the unconditioned reaction) ED$_{50}$ (blocking of the conditioned reaction) |
|---|---|---|
| 3-{2-[4-(8-fluoro-10,11-dihydro-2-methyl-dibenzo[b,f]thiepin-10-yl)-1-piperazinyl]-ethyl}-2-oxazolidinone maleate (Product C) | 14 | 23 |
| 3-{2-[4-(2-chloro-8-fluoro-10,11-dihydro-dibenzo[b,f]thiepin-10-yl)-1-piperazinyl]-ethyl}-2-oxazolidinone maleate (Product D) | 17 | 7.6 |
| 3-{2-[4-(10,11-dihydro-2-methyl-8-methyl-thio-dibenzo[b,f]thiepin-10-yl)-1-piperazinyl]-ethyl}-2-oxazolidinone maleate (Product E) | 25 | 12 |
| Chlorpromazine | 11.8 | 2.5 |

Although the neuroleptic action in C, D and E lies somewhat below that of chlorpromazine, the quality (selectivity) of the neuroleptic action of C, D and E substantially exceeds that of chlorpromazine.

The compounds of the invention, i.e., the compounds of formulas I and Ia can be used in the form of pharmaceutical preparations, which contain them or their salts in admixture with organic or inorganic pharmaceutically inert carriers suitable for enteral and parenteral application such as, for example, water, gelatin, gum arabic, lactose, starches, vegetable oils, polyalkyleneglycols, and the like. The pharmaceutical preparations can be in solid form, for example, tablets, dragees, suppositories or capsules, or in liquid form, for example, as solutions, suspensions or emulsions. The preparations may be sterilized and/or contain additives such as preservatives, stabilizers, wetting or emulsifying agents or salts for varying the osmotic pressure. The pharmaceutical preparations can also contain additional therapeutically active substances.

Preferably, the pharmaceutical dosage forms contain from about 1 to about 200 mg. of a compound of formula I or Ia or an equivalent amount of their respective salts. Preferably, the oral dosage range is between about 0.1 mg/kg/day to about 7.5 mg/kg/day. A preferable dosage range for parenteral preparations is between about 0.01 mg/kg/day to about 0.75 mg/kg/day. It is understood, however, that the above-mentioned ranges can be varied according to the individual needs and the prescription of the practitioner.

As is evident, the compounds of formulas I and Ia and their pharmaceutically acceptable acid addition salts have effects qualitatively similar to those of chlorpromazine, known for its therapeutic uses and properties. Thus, the compounds of the invention demonstrate a pattern of activity associated with neuroleptic agents of known efficacy and safety.

The following Examples further illustrate the invention. All temperatures are in degrees Centigrade, unless otherwise mentioned.

EXAMPLE 1

Preparation of
1-{2-[4-(8-chloro-10,11-dihydro-2-methyl-dibenzo[b,f] thiepin-10-yl)
1-piperazinyl]-ethyl}-2-pyrrolidinone 11 G. of 1-(8-chloro-10,11-dihydro-2-methyl-dibenzo[b,f]thiepin-10-yl)piperazine are heated together with 15.5 g. of potassium carbonate, 0.5 g. of sodium iodide, 11 g. of N-(beta-chloroethyl)-pyrrolidinone and 150 ml. of toluene under reflux conditions over a period of 12 hours. The reaction mixture is evaporated under reduced pressure. The residue is dispersed between water and ether and the ethereal phase is dried over sodium sulfate and evaporated, whereby there is obtained 1-{2-[4-(8-chloro-10,11-dihydro-2-methyl-dibenzo[b,f]thiepin-10-yl)1-piperazinyl]-ethyl}-2-pyrrolidinone, having a melting point of 153°–164°. The maleate melts at 179°–180°.

The starting material 1-(8-chloro-10,11-dihydro-2-methyl-dibenzo[b,f]thiepin-10-yl)-piperazine utilized above can be prepared as follows:

426 G. of potassium hydroxide are dissolved in water at 50° and reacted with 276 g. of 4-chloro-(thiophenol). After 15 minutes, 11 g. of copper powder and 500 g. of 2-iodo-5-methylbenzoic acid are added and the resulting mixture is thereafter heated under reflux conditions over a period of 7 hours. The mixture is filtered warm. The pH of the filtrate is adjusted to 3 with concentrated hydrochloric acid at a temperature of 15° and thereafter diluted with water. The resulting 6-[(4'-chlorophenyl)-thio]-4-methylbenzoic acid is filtered. The product which remains behind comprises crystals having an ocher yellow color, melting at 159°–165°.

583 G. of 6-[(4'-chlorophenyl)thio]-3-methylbenzoic acid, 3.8 l. of absolute methanol and 250 ml. of 96% sulfuric acid are heated together under reflux conditions over a period of 24 hours. Thereafter, the reaction mixture is evaporated under reduced pressure, cooled with ice, poured over aqueous sodium bicarbonate solution and extracted with ether. The ether extract is dried over sodium sulfate and evaporated, whereby there is obtained 6-[(4'-chlorophenyl)thio]-3-methylbenzoic acid methyl ester as brown crystals.

502 G. of 6-[(4'-chlorophenyl)-thio]-3-methylbenzoic acid methyl ester in 4 l. of absolute tetrahydrofuran is reacted under reflux conditions with 580 ml. of a 70% sodium dihydro-bis-(2-methoxyethoxy)-aluminate solution in benzene dropwise, over a period of 30 minutes. After 3 hours of mixing, the reaction mixture is cooled to 4° and mixed with 1.5 l. of benzene. The reaction mixture is hydrolyzed with 1 l. of 2N aqueous hydrochloric acid. The resulting precipitate is dissolved by the addition of concentrated hydrochloric acid. The organic phase is washed with water, dried and evaporated, whereby there is obtained 6-[(4'-chlorophenyl)-thio]-3-methylbenzyl alcohol as a red-brown oil.

446 G. of 6-[(4'-chlorophenyl)-thio]-3-methylbenzyl alcohol in 1 l. of benzene is reacted with 400 g. of thionyl chloride dropwise, and thereafter, heated under reflux conditions. The reaction mixture is thereafter evaporated under reduced pressure, whereby there is obtained 6-[(4'-chlorophenyl)-thio]-3-methylbenzyl chloride as a red-brown oil. 480 G. of 6-[(4'-chlorophenyl)-thio]-3-methylbenzyl chloride, 132 g. of potassium cyanide, 170 ml. of water and 700 ml. of ethanol are heated under reflux conditions for 17 hours. The reaction mixture is thereafter evaporated under reduced pressure, diluted with water and extracted with ether. The ethereal extract is washed with water, dried and evaporated. The dark residue is chromatographed over 1.5 kg. silicon dioxide with benzene. The pure fractions are concentrated together to a about 1 l., diluted with 1 l. of hexane and crystallized at about 0°, whereby 6-[(4'-chlorophenyl)-thio]-3-methyl-phenylacetonitrile is obtained as brown crystals having a melting point of 81°–83°.

374 G. of 6-[(4'-chlorophenyl)-thio]-3-methyl-phenylacetonitrile in 900 ml. of ethanol are heated together with 306 g. of potassium hydroxide in 400 ml. of water under reflux conditions over a period of 15 hours. The reaction mixture is evaporated to dryness under reduced pressure, taken up in water and extracted with ether. The aqueous solution is thereafter cooled with ice, mixed with 500 ml. of hydrochloric acid, and extracted with ether. The ether extract is dried and evaporated. The solid residue is recrystallized from benzene/hexane (2:5), whereby there is obtained 6-[(4'-chlorophenyl)-thio]-3-methylphenyl acetic acid, having a melting point of 107°–109°.

286 G. of 81–84% polyphosphoric acid is reacted with 29.2 g. of 6-[(4'-chlorophenyl)-thio]-3-methylphenyl acetic acid at 120° and stirred for 15 minutes. The hot reaction mixture is poured over ice water and extracted with a mixture of ether/ethyl acetate. The organic phase is thereafter washed with water, aqueous sodium bicarbonate solution and aqueous hydrochloric acid, dried and evaporated, whereby there is obtained 8-chloro-2-methyl-dibenzo[b,f]thiepin-10(11H)-one, which after recrystallization from benzene/hexane has a melting point of 123°–129°.

111.4 G. of 8-chloro-2-methyl-dibenzo[b,f]thiepin-10(11H)-one in 1 l. of absolute benzene are mixed together with 268 ml. of carbethoxypiperazine and within 1 hour at 20°–25° with a solution of 65 ml. of titanium tetrachloride in 500 ml. of absolute benzene. The resulting reaction mixture thereafter is heated under reflux conditions over a period of 20 hours. The reaction mixture is then poured over a mixture of 500 ml. of saturated aqueous sodium bicarbonate solution and 700 ml. of water with strong stirring, subsequently filtered, and washed again with chloroform. After an equilibrium is reached between both phases, the organic phase is dried and evaporated, whereby there is obtained 1-carbethoxy-4-(8-chloro-2-methyl-dibenzo[b,f]thiepin-10-yl)-piperazine as a dark brown viscous oil.

41.5 G. of 1-carbethoxy-4-(8-chloro-2-methyl-dibenzo[b,f]thiepin-10-yl)piperazine are reacted together with 1 l. of absolute diglyme (diethyleneglycoldimethylether) with 26.5 g. of sodium borohydride and stirred at 25° for 30 minutes. The reaction mixture is then mixed dropwise at 20°–30° over a 45-minute period with a solution of 138.6 g. of oxalic acid in 800 ml. of diglyme. The reaction mixture is maintained at 100° for 15 hours. The resulting mixture is evaporated under reduced pressure. The residue is suspended in 1 l. of 2N aqueous sodium hydroxide and extracted with benzene. The benzene extract is washed with water, dried and evaporated, whereby there is obtained 1-carbethoxy-4-(8-chloro-10,11-dihydro-2-methyl-dibenzo[b,f]thiepin-10-yl)piperazine as a red-brown oil, whose nmr and ir spectra are consistent with the proposed structure.

95 G. of 1-carbethoxy-4-(8-chloro-10,11-dihydro-2-methyl-dibenzo[b,f]thiepin-10-yl)-piperazine are stirred together with 1,000 ml. of ethyleneglycol, 77 g. of potassium hydroxide and 10 ml. of water on a bath of 160° for 6 hours. The reaction mixture is poured over ice water and extracted with ether. The ether extract is washed with water, dried and evaporated, whereby 1-(8-chloro-10,11-dihydro-2-methyl-dibenzo[b,f]thiepin-10-yl)-piperazine is obtained as a red-brown viscous oil. After recrystallization from acetone/petroleum ether the product is obtained as crystals having a melting point of 125°–127°.

EXAMPLE 2

In a similar manner to that described in Example 1, from 1-(8-chloro-10,11-dihydro-2-methyl-dibenzo[b,f]thiepin-10-yl)-piperazine and N-(betachloroethyl)oxazolidinone, there is obtained 3-{2-[4-(8-chloro-10,11-dihydro-2-methyl-dibenzo[b,f]thiepin-10-yl)-1-piperazinyl]-ethyl}-2-oxazolidinone, which after recrystallization from ethyl acetate/petroleum ether, has a melting point of 184°–186°. The maleate salt melts after recrystallization from methanol/ether at 174°–175°.

EXAMPLE 3

19 G. of 1-(2-chloro-8-fluoro-10,11-dihydro-dibenzo[b,f]thiepin-10-yl)piperazine are together with 15 g. of pulverized potassium carbonate, 0.3 g of potassium iodide and 150 ml. of toluene reacted with 20.4 g of N-(beta-chloroethyl)-oxazolidinone and heated under reflux conditions for 20 hours. The reaction mixture is poured over water and diluted with benzene. The organic phase is thereafter washed with saturated, aqueous sodium bicarbonate solution and water, dried over magnesium sulfate and evaporated under reduced pressure, whereby there is obtained 3-{2-[4-(2-chloro-8-fluoro-10,11-dihydrodibenzo[b,f]thiepin-10-yl)-1-piperazinyl]-ethyl}-2-oxazolidinone which is treated with maleic acid to form the corresponding maleate which has a melting point of 164°–166°.

The starting material 1-(2-chloro-8-fluoro-10,11-dihydro-dibenzo[b,f]thiepin-10-yl)-piperazine can be prepared according to the following procedure:

A solution of 214 g. of potassium hydroxide and 2 l. of water is reacted with 122 g. of 4-fluoro-(thiophenol) under an atmosphere of nitrogen at 50° and stirred for 15 minutes. After the addition of 3 g. of copper powder and 2.69 g. of 5-chloro-2-iodo-benzoic acid, the reaction mixture is heated under reflux conditions for 7 hours. The entire mixture is filtered warm and the filtrate acidified with hydrochloric acid. The resulting precipitate is filtered, washed neutral with water and evaporated under reduced pressure, whereby there is obtained 3-chloro-6-[(4'-fluorophenyl)-thio]-benzoic acid, having a melting point of 176°–177°.

264 G. of 3-chloro-6-[(4'-fluorophenyl)-thio]-benzoic acid in 2 l. of absolute tetrahydrofuran is mixed together dropwise under an atmosphere of nitrogen with 450 ml. of a 70% sodium dihydro-bis-(2-methoxyethoxy)-aluminate solution in benzene under reflux conditions, and thereafter boiled under reflux conditions for an additional 30 minutes. After cooling of the reaction mixture to 10°, it is acidified with a liter of 3N hydrochloric acid, then treated with concentrated hydrochloric acid and extracted with ether. The organic phase is washed with water, 2N aqueous sodium hydroxide solution and then with water until a neutral reaction is obtained. This mixture is dried over sodium sulfate, filtered and evaporated, whereby there is obtained 3-chloro-6-[(4'-fluorophenyl)-thio]-benzyl alcohol as a brown oil.

244 G. of 3-chloro-6-[(4'-fluorophenyl)-thio]-benzyl alcohol is dissolved in 800 ml. of absolute benzene and brought to the reflux temperature. This solution is reacted with 97.5 ml. of thionyl chloride over a period of 40 minutes and thereafter boiled for an additional 30 minutes. The reaction mixture is evaporated under reduced pressure. The residue is treated 3 times with benzene and evaporated, whereby there is obtained 3-chloro-6-[(4'-chlorophenyl)-thio]-benzyl chloride as a brown oil.

81 G. of potassium cyanide in 160 ml. of water is reacted with 255 g. of 3-chloro-6-[(4'-fluorophenyl)-thio]-benzyl chloride in 400 ml. of ethanol and heated at reflux for 9 hours. The ethanol is evaporated under reduced pressure. The residue is diluted with water and extracted with ether. The ether extract is washed with water, dried over sodium sulfate and evaporated, whereby there is obtained 3-chloro-6-[(4'-fluorophenyl)-thio]-phenylacetonitrile as a dark brown oil.

234 G. of 3-chloro-6-[(4'-fluorophenyl)-thio]-phenylacetonitrile, 500 ml. of ethanol, 254 g. of potassium hydroxide and 500 ml. of water are heated together under reflux conditions over a period of 18 hours. The ethanol is removed by evaporation under reduced pressure. The residue is dissolved in water, and the neutral portion is extracted with ether. The aqueous solution is acidified with concentrated hydrochloric acid and extracted with benzene. The benzene phase is washed with water, dried over sodium sulfate, filtered and evaporated under reduced pressure, whereby there is obtained 3-chloro-6-[(4'-fluorophenyl)thio]-phenylacetic acid as dark brown oil. After recrystallization from benzene/hexane, the product is obtained as crystals having a melting point of 93°.

990 G. of polyphosphoric acid is heated under an atmosphere of nitrogen to 120°, quickly reacted with 99 g. of 3-chloro-6-[(4'-fluorophenyl)-thio]-phenylacetic acid and stirred for 5 minutes at 120°. After the addition of crushed ice, the reaction mixture is extracted with chloroform. The organic phase is washed with water, aqueous sodium hydroxide and water, dried over sodium sulfate and evaporated, whereby there is obtained 2-chloro-8-fluoro-dibenzo[b,f] thiepin-10(11H)-one, having a melting point of 132°.

60 G. of 8-chloro-8-fluoro-dibenzo[b,f]thiepin-10(11H)-one are suspended in 330 ml. of ethanol and reacted with 13.9 g. of sodium borohydride. The mixture is stirred at room temperature for 1 hour and thereafter, treated with water and extracted with ether. The organic phase is washed with water, dried over magnesium sulfate and evaporated, whereby there is obtained 2-chloro-8-fluoro-10,11-dihydro-dibenzo[b,f]thiepin-10-ol having a melting point of 90°.

58.3 G. of 2-chloro-8-fluoro-10,11-dihydro-dibenzo[b,f]thiepin-10-ol 300 ml. of benzene and 21 g. of finely pulverized calcium chloride are saturated with hydrochloric acid over a period of 2 hours at 15°. The resulting precipitate is filtered, washed with benzene and evaporated under reduced pressure, whereby there is obtained 2,10-dichloro-8-fluoro-10,11-dihydro-dibenzo[b,f]thiepin as white crystals, having a melting point of 84°-85°.

24 G. of 2,10-dichloro-8-fluoro-10,11-dihydro-dibenzo[b,f]thiepin in 80 ml. of chloroform are heated together with 38.4 g. of 1-carbethoxy-piperazine under reflux conditions for 20 hours. The reaction mixture is poured over ice water and extracted with chloroform. The organic phase is dried over magnesium sulfate and evaporated under reduced pressure, whereby there is obtained oily 1-carbethoxy-4-(2-chloro-8-fluoro-10,11-dihydro-dibenzo[b,f]thiepin-10-yl)-piperazine.

24.5 G. of 1-carbethoxy-4-(2-chloro-8-fluoro-10,11-dihydro-dibenzo[b,f]thiepin-10-yl)-piperazine, 350 ml. of ethyleneglycol, 19 g. of potassium hydroxide and 1.5 ml. of water are heated together at 160° for 1 hours. The reaction mixture is poured over water and extracted with chloroform. The organic phase is washed with water, dried over magnesium sulfate and evaporated under reduced pressure, whereby there is obtained 1-(2-chloro-8-fluoro-10,11-dihydro-dibenzo[b,f]thiepin-10-yl)-piperazine as a thick oil.

EXAMPLE 4

In a similar manner to that described in Example 3, from 1-(2-chloro-7-fluoro-10,11-dihydro-dibenzo[b,f]-thiepin-10-yl)-piperazine and N-(beta-chloroethyl)-oxazolidinone, there is obtained 3-{2-[4-(2-chloro-7-fluoro-10,11-dihydro-dibenzo[b,f]thiepin-10-yl)-1-piperazinyl]-ethyl}-2-oxazolidinone, whose maleate after recrystallization from ethanol/ether, has a melting point of 172°-174°.

The starting material 1-(2-chloro-7-fluoro-10,11-dihydro-dibenzo[b,f]-thiepin-10-yl)-piperazine can be obtained from 5-chloro-2-iodo-benzoic acid and 3-fluoro-(thiophenol) in a similar manner to that described in Example 3. Utilizing that procedure, the following intermediates are formed:

3-chloro-6-[(3'-fluorophenyl)-thio]-benzoic acid, having a melting point of 171°-173°;

3-chloro-6-[(3'-fluorophenyl-thio]-benzyl alcohol as a brown oil;

3-chloro-6-[(3'-fluorophenyl)-thio]-benzyl chloride as a brown oil;

3-chloro-6-[(3'-fluorophenyl)-thio]-phenylacetonitrile;

3-chloro-6-[(3'-fluorophenyl)-thio]-phenyl acetic acid, having a melting point of 124°-126° after recrystallization from acetone/hexane;

2-chloro-7-fluoro-dibenzo[b,f]thiepin-10(11H)-one, having a melting point of 117.5°-118.5°;

2-chloro-7-fluoro-10,11-dihydro-dibenzo[b,f]thiepin-10-ol, having a melting point of 98°-99°;

2,10-dichloro-7-fluoro-10,11-dihydro-dibenzo[b,f]-thiepin, having a melting point of 119°-120°; and

1-carbethoxy-4-(2-chloro-7-fluoro-10,11-dihydro-dibenzo[b,f]thiepin-10-yl)-piperazine, having a melting point of 117°-118°.

The 1-(2-chloro-7-fluoro-10,11-dihydro-dibenzo[b,f]thiepin-10-yl)-piperazine is obtained as an oil which after usual work-up can be obtained in pure form.

EXAMPLE 5

17.6 g of 10-chloro-8-fluoro-10,11-dihydro-2-methyldibenzo[b,f]thiepin are heated for 20 hours under reflux conditions together with 27.3 g of 3-{2-(1-piperazinyl)-ethyl]-2-oxazolidinone in 10 ml of chloroform. After evaporation of the chloroform, the residue is mixed with ice, benzene and aqueous sodium hydroxide solution and again mixed well. The benzene phase is acidified with 6 N aqueous hydrochloric acid and maintained in an ice bath for 30 minutes. The precipitate, which is formed, is filtered, made alkaline with aqueous sodium hydroxide solution and taken up in benzene. The benzene phase is dried over sodium sulphate and evaporated, whereby 3-{2-[4-(8-fluoro-10,11-dihydro-2-methyl-dibenzo [b,f]thiepin-10-yl)-1-piperazinyl]-ethyl}-2-oxazolidinone is obtained, which is converted into the corresponding dihydrochloride by reaction with ethanolic hydrochloric acid. The dihydrochloride melts at 210°(dec;).

The starting material 10-chloro-8-fluoro-10,11-dihydro-2-methyl-dibenzo[b,f]thiepin can be prepared as follows:

A solution of 474.5 g. of potassium hydroxide in 3.6 l. of water is reacted under an atmosphere of nitrogen at 50° with 217 ml. of 4-fluoro-(thiophenol) and mixed at room temperature for 15 minutes. After the addition of 1 g. of copper powder and 536 g. of 2-iodo-5-methylbenzoic acid, the mixture is heated under reflux conditions for 7 hours. The reaction mixture is filtered hot, acidified with hydrochloric acid and filtered again. The residue is washed neutral with water and evaporated under reduced pressure, whereby 3-methyl-6-[(4'-fluorophenyl)thio]-benzoic acid is obtained and has a melting point of 166°–167°.

300 G. of 3-methyl-6-[(4'-fluorophenyl)-thiol]-benzoic acid in 2 l. of absolute tetrahydrofuran is reacted dropwise under a atmosphere of nitrogen and under reflux conditions with 780 ml. of a 70% sodium dihydro-bis-(2-methoxyethoxy)-aluminate solution in benzene and heated for an additional 1 hour under reflux conditions. The reaction mixture is cooled to 4°, acidified dropwise with 1,300 ml. of 3N hydrochloric acid, then mixed with concentrated hydrochloric acid and extracted with benzene. The organic phase is washed with water, dried over sodium sulfate, filtered and evaporated, whereby there is obtained 3-methyl-6-[(4'-fluorophenyl)-thio]-benzyl alcohol as a yellow oil.

337 G. of 3-methyl-6-[(4'-fluorophenyl)-thio]-benzyl alcohol is dissolved in 1 l. of absolute benzene and maintained at reflux temperature. The solution is treated dropwise with 190 ml. of thionyl chloride and heated for an additional 45 minutes. This reaction mixture is evaporated under reduced pressure. The residue is again extracted with benzene, the benzene solution is evaporated, whereby there is obtained 3-methyl-6-[(4'-fluorophenyl)-thio]-benzyl chloride as a brown oil.

115 G. of potassium cyanide in 150 ml. of water are heated together with 344 g. of 3-methyl-6-[(4'-fluorophenyl)-thio]-benzyl chloride in 450 ml. of ethanol under reflux conditions over a period of 10 hours. The ethanol is thereafter distilled under reduced pressure. The residue is diluted water water and extracted with benzene. The benzene phase is again washed with water, dried over sodium sulfate and evaporated, whereby there is obtained 3-methyl-6-[4'-fluorphenyl)-thio]-phenylacetonitrile as a dark brown oil.

106 G. of 3-methyl-6-[(4'-fluorophenyl)-thio]-phenylacetonitrile, 300 ml. of ethanol, 100 g. of potassium hydroxide and 300 ml. of water are heated together under reflux conditions over a period of 5 hours. Thereafter, the ethanol is evaporated under reduced pressure. The residue is dissolved in water and the neutral portion extracted with benzene. The aqueous solution is acidified with concentrated hydrochloric acid and extracted with ethyl acetate. The organic phase is washed with water, dried over sodium sulfate, filtered and evaporated under reduced pressure, whereby there is obtained 3-methyl-6-[(4'-fluorophenyl)thio]-phenyl acetic acid as a dark brown oil, which after recrystallization from benzene/hexane, has a melting point of 117°.

1,810 G. of polyphosphoric acid is heated under an atmosphere of nitrogen to 128°, then quickly there is mixed therewith 173.6 g. of 3-methyl-6-[(4'-fluorophenyl)-thio]-phenyl acetic acid and the mixture is stirred at 120°–130° for 10 minutes. After the addition of crushed ice, the mixture is extracted with benzene. The organic phase is again washed with water with a saturated aqueous sodium carbonate solution, dried over sodium sulfate and evaporated, whereby there is obtained 8-fluoro-2-methyl-dibenzo[b,f]-thiepin-10(11H)-one, which has a melting point of 103°–104°.

103 G. of 8-fluoro-2-methyl-dibenzo[b,f]-thiepin-10(11H)-one is suspended in 550 ml. of ethanol and mixed with 24.3 g. of sodium borohydride. The reaction mixture is heated for about 10 minutes under reflux conditions. The reaction mixture, after the addition of water, is extracted with chloroform. The organic phase is again washed with water, dried over sodium sulfate and evaporated, whereby there is obtained 8-fluoro-10,11-dihydro-2-methyl-dibenzo[b,f]-thiepin-10-ol as an oil.

103 G. of 8-fluoro-10,11-dihydro-2-methyl-dibenzo[b,f]thiepin-10-one, 500 ml. of benzene and 38.4 g. of finely pulverized calcium chloride are saturated with hydrochloric acid gas at 15° and stirred overnight. The residue is filtered, washed with benzene and evaporated under reduced pressure, whereby there is obtained 10-chlor-8-fluoro-10,11-dihydro-2-methyl-dibenzo[b,f]-thiepin, having a melting point of 63°–64°.

EXAMPLE 5a

In a similar manner to that described in example 5, from 10-chloro-10,11-dihydro-2-methyl-8-(methylthio)dibenzo[b,f]thiepin and 3-[2-(1-piperazinyl)ethyl]-2-oxazolidinone, there is obtained 3-{2-[4-(10,11-dihydro-2-methyl-(8-methylthio)dibenzo[b,f]thiepin-10-yl)-1-piperazinyl]-ethyl}-2-oxazolidinone having a melting point of 120-14 122°. The maleate salt melts at 156°–158°.

The staring material 10-chloro-10,11-dihydro-2-methyl-8-(methylthio)dibenzo[b,f]thiepin can be prepared in a similar manner to that described in example 5.

EXAMPLE 6

14 g of 10-chloro-10,11-dihydro-3-methoxy-(8-methylthio)dibenzo[b,f]thiepin are kept for 16 hours at reflux conditions together with 20.9 g of 3-[2-(1-piperazinyl)ethyl]-2-oxazolidinone in 75 ml of chloroform. The solvent is distilled off and the residue treated with 1 N aqueous sodium hydroxide solution and ether. The insoluble parts are filtered off. The filter cake is chromatographed over aluminum oxide with chloroform. The so-obtained purified 3-{2-[4-(10,11-dihydro-3-methoxy-(8-methylthio)dibenzo[b,f]thiepin-yl)-1-piperazinyl]-ethyl}-2-oxazolidinone is converted into the corresponding dihydrochloride by treatment with ethanolic hydrochloric acid. The dihydrochloride is recrystallised from ethanol and ether and melts at 217°–219° (dec.).

The Starting material 10-chloro-10,11-dihydro-3-methoxy-8-(methylthio)dibenzo[b,f]thiepin can be prepared as follows:

150 G. of 4-methoxy-anthranillic acid is suspended in 2 l. of water and 80 ml. of concentrated hydrochloric acid 0°. To this mixture is added dropwise with stirring, a solution of 62 g. of sodium nitrite in 130 ml. of water at 0°–5° over a period of 30 minutes. The resulting diazonium salt solution is stirred at 0°–5° for an additional 15 minutes. Subsequently, there is added a solution of 164 g. of potassium iodide in 700 ml. of 5N sulfuric acid at a temperature of 3°–6° over a 45 minute period. The resulting mixture is mixed at room temperature for 30 minutes and subsequently heated slowly at reflux temperature. After heating at reflux for 2 hours, the mixture is cooled to room temperature. The separated brown crystals are filtered and washed neutral with water. The filter cake is dried under reduced pressure, whereby there is obtained as brown crystals 2-iodo-4-methoxy-benzoic acid having a melting point of 174°.

411 G. of 2-iodo-4-methoxy-benzoic acid, 4 l. methanol and 400 ml. of concentrated sulfuric acid are heated at reflux for 4 hours. The solution is then evaporated under reduced pressure, treated with water, and extracted with ether. The organic phase is then washed with aqueous sodium thiosulfate solution and aqueous bicarbonate solution and subsequently dried over sodium sulfate. The solution is filtered, evaporated under reduced pressure and distilled. There is obtained the 2-iodo-4-methoxy-benzoic acid methyl ester, having a boiling point of 95°–98°/0.04 mm.

205 G. of 2-iodo-4-methoxy-benzoic acid methyl ester, 400 ml. of methanol, 390 ml. of water and 95 g. of potassium hydroxide are reacted for 30 minutes at 48°. Subsequently, the solution is concentrated under reduced pressure and acidified with aqueous hydrochloric acid. The resulting yellow crystalline 2-iodo-4-methoxy-benzoic acid is filtered, washed neutral with water and dried. The resulting compound melts at 185°.

A solution of 170 g. of potassium hydroxide in 1.6 l. of water is reacted under an atmosphere of nitrogen with 102 g. of 4-(methylthio)-(thiophenol) at 50°. The resulting mixture is subsequently stirred for an additional 15 minutes. The mixture is reacted with 2.4 g. of copper powder and 180 g. of 2-iodo-4-methoxy-benzoic acid and heated under reflux conditions for 7 hours. The reaction mixture is filtered hot, acidified with concentrated hydrochloric acid, cooled and filtered. The residue is washed with water and dried under reduced pressure, whereby there is obtained 4-methoxy-6-{[4'-(methylthio)-phenyl]-thio}benzoic acid having a melting point of 202°–203°.

190 G. of 4-methoxy-6-{[4'-(methylthio)-phenyl]thio}-benzoic acid in 1.8 l. of absolute tetrahydrofuran was treated dropwise under an atmosphere of nitrogen and under reflux conditions with 850 ml. of a 70% solution of sodium dihydro-bis-(2-methoxy-ethoxy)-aluminate solution in benzene. The reaction mixture is then heated under reflux conditions for an additional 30 minutes. After cooling to 5°, the reaction mixture is acidified with 500 ml. of 3N hydrochloric acid and with concentrated hydrochloric acid and thereafter extracted with ether. The organic phase is washed with water, 2N aqueous sodium hydroxide solution and again with water and dried over sodium sultate, filtered and evaporated, whereby there is obtained 4-methoxy-6-{[4'-(methylthio)-phenyl]thio}-benzyl alcohol as a brown oil.

165 G. of 4-methoxy-6-{[4'-(methylthio)-phenyl]thio}-benzyl alcohol are dissolved in 500 ml. of absolute benzene and heated under reflux conditions. The resulting solution is treated dropwise over a period of 45 minutes with 62 ml. of thionyl chloride and subsequently heated over a period of 30 minutes. The reaction mixture is evaporated under reduced pressure. The residue is extracted three times with benzene. From the benzene solution there is obtained 4-methoxy-6{[4'-(methylthio)-phenyl] thio}-benzyl chloride as a dark brown oil.

51 G. of potassium cyanide in 110 ml. of water are heated with 186 g. of 4-methoxy-6-{[4'-(methylthio)-phenyl]-thio}-benzyl chloride in 270 ml. of ethanol under reflux conditions over a period of 9 hours. The ethanol is distilled under reduced pressure, thereafter the residue is diluted with water and extracted with ether. The ethereal extract is washed with water, dried over sodium sulfate and evaporated, whereby there is obtained 4-methoxy-6-{[4'-(methylthio)-phenyl]-thio}-phenylacetonitrile as a dark brown oil 160 G. of 4-methoxy-6-{4'-(methylthio)-phenyl]-thio}-phenylacetonitrile, 330 ml. of ethanol, 162 g. of potassium hydroxide and 330 ml. of water are heated under reflux conditions for 8 hours. Thereafter, the ethanol is evaporated under reduced pressure. The resulting residue is washed twice with 2 l. of water. The aqueous solution is extracted with ether and the ether extract is discarded. The aqueous solution is cooled and acidified with concentrated hydrochloric acid. The solution thereafter is extracted with benzene and the benzene phase washed with water, dried over sodium sulfate, filtered and evaporated, whereby there is obtained 4-methoxy-6{[4'-(methylthio)-phenyl]-thio}-phenylacetic acid which upon recrystallization from benzene/hexane has a melting point of 125°.

29.3 G. of 4-methoxy-6{[4'-(methylthio)-phenyl]-thio}-phenylacetic acid is stirred with 150 g. of polyphosphoric acid in 600 ml. of toluene under reflux conditions for 17 hours. The reaction mixture is cooled to about 60° and the toluene solution is decanted. The residue is treated with toluene and heated with stirring. The aqueous residue is treated with ice and water and extracted with toluene. The so-obtained toluene solution is thereafter treated with water and aqueous sodium hydroxide and washed with aqueous sodium hydroxide solution, dried over sodium sulfate and concentrated under reduced pressure, whereby there is obtained 3-methoxy-8-(methylthio)-dibenzo[b,f]thiepin-10(11H)-one as a red oil. Upon recrystallization from acetone/hexane there is obtained from the red oil a crystalline product having a melting point of 127°.

17.8 G. of 3-methoxy-8-(methylthio)-dibenzo[b,f]-thiepin-10(11H)-one is suspended in 150 ml. of ethanol and reacted with 38 g. of sodium borohydride. The reaction mixture is stirred for 90 minutes, and subsequently treated with water and extracted with ether. The organic phase is washed with water, dried over magnesium sulfate and evaporated, whereby there is obtained 10,11-dihydro-3-methoxy-8-(methylthio)-dibenzo[d,f]thiepin-10-ol having a melting point of 122°–124°.

15.7 G. of 10,11-dihydro-3-methoxy-8-(methylthio)-dibenzo[b,f]thiepin-10-ol, 250 ml. of benzene and 6 g. of finely pulverized calcium chloride are saturated with hydrochloric acid gas over a period of 2½ hours at 15° and subsequently stirred for an additional 3 hours. After the addition of 0.8 g. of activated charcoal, the mixture is filtered and washed with benzene. The benzene phase is evaporated under reduced pressure, whereby there is obtained 10-chloro-10,11-dihydro-3- methoxy-8-(methylthio)-dibenzo[b,f]thiepin, having a melting point of 120°–123°.

EXAMPLE 7

Preparation of
1-{2-[4-(10,11-dihydro-3-methoxy-8-methylthio-dibenzo[b,f]thiepin-10-yl)-1-piperazinyl]-ethyl}-2-pyrrolidinone 11 G. of 1-(10,11-dihydro-3-methoxy-8-methylthio-dibenzo[b,f]thiepin-10-yl)-piperazine are heated together with 15 g. of potassium carbonate, 0.5 g. of sodium iodide, 11 g. of N-(β-chloroethyl)-2-pyrrolidinone and 100 ml. of toluene under reflux conditions for 17 hours. Then, the mixture is evaporated under reduced pressure. The residue is partitioned between water and ether, and the ethereal phase dried over sodium sulfate and evaporated. The residue obtained is chromatographed with chloroform over aluminum oxide. The 1-{2-[4-(10,11-dihydro-3-methoxy-8-methylthio-dibenzo[b,f]thiepin-10-yl)-1-piperazinyl]-ethyl}-2-pyrrolidinone thus obtained is converted into the corresponding dihydrochloride by reaction with hydrogen chloride. The resulting dihydrochloride melts at 202°C.

The 1-(10,11-dihydro-3-methoxy-8-methylthio-dibenzo[b,f]-thiepin-10-yl)-piperazine used as the starting material can be prepared as follows:

24 G. of 10-chloro-10,11-dihydro-3-methoxy-8-methylthio-dibenzo[b,f]thiepin in 100 ml. of chloroform are heated with 55 ml. of 1-carbethoxypiperazine under reflux conditions for 20 hours. The mixture is poured on to ice/water and extracted with chloroform. The organic phase is dried over magnesium sulfate and evaporated under reduced pressure, whereby there is obtained crude 1-carbethoxy-4-(10,11-dihydro-3-methoxy-8-methylthiodibenzo[b,f]thiepin-10-yl)-piperazine.

61 G. of 1-carbethoxy-4-(10,11-dihydro-3-methoxy-8-methylthio-dibenzo[b,f]thiepin-10-yl)-piperazine, 600 ml. of ethylene glycol, 25 g. of potassium hydroxide and 2.7 ml. of water are heated at 160°C. for a period of 2 hours. Then, the mixture is poured on to water and extracted with benzene. The organic phase is washed with water, dried over magnesium sulfate and evaporated under reduced pressure, whereby there is obtained 1-(10,11-dihydro-3-methoxy-8-methylthio-dibenzo[b,f]thiepin-10-yl)-piperazine.

EXAMPLE 8

Preparation of
3-{2-[4-(8-chloro-10,11-dihydro-3-methoxy-dibenzo[b,f]thiepin-10-yl)-1-piperazinyl]-ethyl}-2-oxazolidinone In an analogous manner to that described in Example 5, 3- 2-[4-(8-chloro-10,11-dihydro-3-methoxy-dibenzo[b,f]thiepin-10-yl)-1-piperazinyl]-ethyl -2-oxazolidinone (which, after recrystallization from ethyl acetate/petroleum ether, melts at 182°–185°C.) is prepared from 8,10-dichloro-10,11-dihydro-3-methoxy-dibenzo[b,f]thiepin and 3-[2-(1-piperazinyl)-ethyl]-2-oxazolidinone. After recrystallization from ethanol/diethyl ether, the dimethanesulfonate melts at 148°–150°C.

The 8,10-dichloro-10,11-dihydro-3-methoxy-dibenzo[b,f] thiepin used as the starting material can be prepared in the same manner as described in Example 6 starting from 2-iodo-4-methoxy-benzoic acid and 4-chloro-thiophenol. The following intermediates are obtained in the reaction:

4-methoxy-2-[(4-chlorophenyl)-thio]benzoic acid; melting point 195°–198°C.;
4-methoxy-2-[(4-chlorophenyl)-thio]-benzyl alcohol; melting point 69°–70°C.;
4-methoxy-2-[(4-chlorophenyl)-thio]-benzyl chloride; melting point 61°–64°C.;
4-methoxy-2-[(4-chlorophenyl)-thio]-phenylacetonitrile; (brown oil);
4-methoxy-2[(4-chlorophenyl)-thio]-phenylacetic acid; melting point 117°–118°C.;
8-chloro-3-methoxy-dibenzo[b,f]thiepin-10(11H)-one; melting point 132°–134°C.;
8-chloro-10,11-dihydro-3-methoxy-dibenzo[b,f]thiepin-10-ol; melting point 105°–107°C.

The 8,10-dichloro-10,11-dihydro-3-methoxy-dibenzo[b,f]thiepin obtained melts at 100°–102°C.

EXAMPLE 9

Preparation of
1-{2-[4-(10,11-dihydro-3-methoxy-8-methylthiodibenzo[b,f]thiepin-10-yl)-1-piperazinyl]-ethyl}-3-methyl-2-imidazolidinone In an analogous manner to that described in Example 7, 1-{2-[4-(10,11-dihydro-3-methoxy-8-methylthio-dibenzo[b,f]thiepin-10-yl)-1-piperazinyl]-ethyl}-3-methyl-2-imidazolidinone (whose dihydrochloride melts at 191°C.) is prepared from 1-(10,11-dihydro-3-methoxy-8-methylthio-dibenzo[b,f]thiepin-10-yl)-piperazine and 1-(2-chloroethyl)-3-methyl-2-imidazolidinone.

EXAMPLE 10

Preparation of
1-{2-[4-(10,11-dihydro-3-methoxy-8-methylthiodibenzo[b,f]thiepin-10-yl)-1-piperazinyl]-ethyl}-2-benzimidazolidinone In an analogous manner to that described in Example 7, 1-{2-[4-(10,11-dihydro-3-methoxy-8-methylthio-dibenzo[b,f]thiepin-10-yl)-1-piperazinyl]-ethyl}-2-benzimidazolidnone (whose dihydrochloride melts at 250°C.) is prepared from 1-(10,11-dihydro-3-methoxy-8-methylthio-dibenzo[b,f]thiepin-10-yl)- piperazine and N-(2-chloroethyl)-2-benzimidazolidinone.

EXAMPLE 11

Preparation of
1-{2-[4-(10,11-dihydro-3-methoxy-8-methylthiodibenzo[b,f]thiepin-10-yl)-1-piperazinyl]ethyl}-2-piperidinone In an analogous manner to that described in Example 7, 1-{2-[4-(10,11-dihydro-3-methoxy-8-methylthio-dibenzo[b,f]thiepin-10-yl)-1-piperazinyl]-ethyl}-2-piperidinone (whose dihydrochloride melts at 199°C.) is prepared from 1-(10,11-dihydro-3-methoxy-8-methylthio-dibenzo[b,f]thiepin-10-yl)-piperazine and N-(2-chloroethyl)-2-piperidinone hydrochloride.

EXAMPLE 12

Preparation of
3-{3-[4-(10,11-dihydro-3-methoxy-8-methylthiodibenzo[b,f]thiepin-10-yl)-1-piperazinyl]-propyl}-2-oxazolidinone In an analogous manner to that described in Example 7, 3-{3-[4-(10,11-dihydro-3-methoxy-8-methylthiodibenzo[b,f]thiepin 10-yl)-1-piperazinyl]-propyl}-2-oxazolidinone (whose dihydrochloride melts at 180°–181°C.) is prepared from 1-(10,11-dihydro-3-methoxy-8-methylthio-dibenzo[b,f]thiepin-10yl)piperazine and N-(3-chloropropyl)-2-oxazolidinone.

EXAMPLE 13

Preparation of
3-{2-[4-(10,11-dihydro-3-methoxy-8-methylthiodibenzo[b,f]thiepin-10-yl)-1-piperazinyl]-ethyl}-2-thiazolidinone In an analogous manner to that described in Example 7, 3-{2-[4-(10,11-dihydro-3-methoxy-8-methylthiodibenzo[b,f]thiepin 10-yl)-1-piperazinyl]-ethyl}-2-thiazolidinone (whose dihydrochloride melts at 211°–212°C.) is prepared from 1-(10,11-dihydro-3-methoxy-8-methylthio-dibenzo[b,f]thiepin-10-yl)-piperazine and N-(2-chloroethyl)-2-thiazolidinone.

EXAMPLE 14

Preparation of
3-{2-[4-(8-chloro-2-methyl-dibenzo[b,f]thiepin-10-yl)-1-piperazinyl]-ethyl}-2-oxazolidinone 27.4 G. of 8-chloro-2-methyl-dibenzo[b,f]thiepin-10(11H)-one, 400 ml. of absolute benzene and 40 g. of 3-[2-(1-piperazinyl)-ethyl]-2-oxazolidinone are stirred under an atmosphere of argon at 20°C. To the mixture, there are added dropwise over a period of 60 minutes, 9.3 ml. of titanium tetrachloride in 200 ml. of absolute benzene. The mixture is subsequently heated at reflux for 3.5 hours and, after cooling to about 40°C., poured on to a saturated, aqueous sodium bicarbonate solution and stirred for an additional 30 minutes. The suspension obtained is filtered and the benzene phase separated. The aqueous phase is back-extracted with 100 ml. of benzene. The combined benzene extracts are washed with water, dried over magnesium sulfate, filtered and evaporated. By recrystallization from acetonitrile, there is recovered from the residue still unchanged 8-chloro-2-methyldibenzo[b,f]thiepin-10(11H)-one. The mother liquor is evaporated and the residue recrystallized from benzene, whereby there is obtained 3-{2-[4-(8-chloro-2-methyl-dibenzo[b,f]thiepin-10-yl)-1-piperazinyl]-ethyl}-2-oxazolidinone which melts at 194°–196°C.

EXAMPLE 15

Preparation of
3-{2-[4-(8-chloro-10,11-dihydro-2-methyl-dibenzo[b,f]thiepin-10-yl)-1-piperazinyl]-ethyl}-2-oxazolidinone 1.0 G. of 3-{2-[4-(8-chloro-2-methyl-dibenzo[b,f]thiepin10-yl)-1-piperazinyl]-ethyl}-2-oxazolidinone is stirred at room temperature with 50 ml. of diethyleneglycol dimethyl ether (diglyme) and 0.6 g. of sodium borohydride for 30 minutes under an atmosphere of argon. Thereafter, a solution of 2.8 g. of oxalic acid ($C_2H_2O_4 \cdot 2H_2O$) in 15 ml. of diglyme is added dropwise at 20°–30°C. The mixture is stirred at 100°C. for 4 hours, and subsequently evaporated under reduced pressure. The residue is taken up in 2N sodium hydroxide and water, and extracted three times with 100 ml. of benzene each time. The combined benzene phases are washed with water, dried over magnesium sulfate, filtered and concentrated. The crystalline residue is recrystallized from ethyl acetate/petroleum ether (low boiling), whereby there is obtained 3-{2-[4-(8-chloro-10,11-dihydro-2-methyl-dibenzo[b,f]thiepin-10-yl)-1-piperazinyl]-ethyl}-2-oxazolidinone, having a melting point of 184°–186°C. The maleate crystallizes from methanol/ether and melts at 174°–175°C.

EXAMPLE 16

Preparation of
3-{2-[4-(8-fluoro-10,11-dihydro-3-methyl-dibenzo[b,f]thiepin-10-yl)-1-piperazinyl]-ethyl}-2-oxazolidinone 10.6 g. of 10-chloro-8-fluoro-10,11-dihydro-3-methyldibenzo[b,f]thiepin are heated at reflux together with 200 ml. of chloroform and 22.8 g. of 3-[2-(1-piperazinyl)-ethyl]-2-oxazolidinone for 30 hours. Thereafter, the mixture is evaporated under reduced pressure, and the residue is worked up as described in Example 5. The insoluble base is recrystallized from ethanol, whereby there is obtained 3-{2-[4-(8-fluoro-10,11-dihydro-3-methyl-dibenzo[b,f]thiepin-10-yl)-1-piperazinyl]-ethyl}-2-oxazolidinone which melts at 173°–175°C. The maleate crystallizes from acetone/ether and has a melting point of 147°–149°C.

The 10-chloro-8-fluoro-10,11-dihydro-3-methyldibenzo[b,f]thiepin used as the starting material can be prepared in an analogous manner to that described in Example 3 starting from 2-iodo-4-methyl-benzoic acid and 4-fluoro-thiophenol. The following intermediates are obtained in the reaction:

4-methyl-2-(4'-fluorophenyl)-thio]acid; melting point 185°–186°C.;
4-methyl-2-[(4'-fluorophenyl)-thio]-benzyl alcohol; (orange-colored oil);
4-methyl-2-[4'-fluorophenyl)-thio[-benzyl chloride; (red-brown oil);
4-methyl-2-[(4'-fluorophenyl)-thio[-phenylacetonitrile; (brown oil);
4-methyl-2-[4'-fluorophenyl)-thio]-phenylacetic acid; melting point 135°–137°C. after recrystallization from acetone/petroleum ether (low boiling);
8-fluoro-3-methyl-dibenzo[b,f]thiepin-10(11H)-one; melting point 96°–99°C. after recrystallization from ethanol;
8-fluoro-3-methyl-10,11-dihydro-dibenzo[b,f]thiepin-10-ol; (brown oil).

The 10-chloro-8-fluoro-10,11-dihydro-3-methyldibenzo[b,f]thiepin is obtained as a brown oil which crystallizes on standing.

EXAMPLE 17

Preparation of
3-{2-[4-(2-chloro-10,11-dihydro-8-methylthiodibenzo[b,f]thiepin-10-yl)-1-piperazinyl]-ethyl}-2-oxazolidinone In an analogous manner to that described in Example 16, 3-{2-[4-(2-chloro-10,11-dihydro-8-methylthiodibenzo[b,f]thiepin 10-yl)-1-piperazinyl]-ethyl}-2-oxazolidinone (which, after recrystallization from ethyl acetate/petroleum ether (low boiling), melts at 90°–92°C.) is prepared from 2,10-dichloro-10,11-dihydro-8-methylthio-dibenzo[b,f]thiepin and 3-[2-(1-piperazinyl)-ethyl]2-oxazolidinone. The salt formed with 1.8 moles of hydrogen chloride melts at 203°–205°C.

The 2,10-dichloro-10,11-dihydro-8-methylthiodibenzo[b,f]thiepin used as the starting material can be prepared in an analogous manner to that described in Example 3 starting from 2-iodo-5-chloro-benzoic acid and 4-methylthio-thiophenol. The following intermediates are obtained in the reaction:

5-chloro-2-[4'-methylthio-phenyl)thio]-benzoic acid; melting point 170°–180°C.;

5-chloro-2-[(4'-methylthio-phenyl)-thio]-benzyl alcohol; (red-brown oil);

5-chloro-2-[(4'-methylthio-phenyl)-thio]-benzyl chloride; (red-brown oil);

5-chloro-2-[(4'-methylthio-phenyl)-thio]-phenylacetonitrile; (dark, red-brown oil);

5-chloro-2-[4'-methylthio-phenyl)-thio]-phenylacetic acid; melting point 112°–113°C. after recrystallization from ethyl acetate/petroleum ether (low boiling);

2-chloro-8-methylthio-dibenzo[[b,f]thiepin-10(11H)-one; melting point 173°–175°C. after recrystallization from xylene;

2-chloro-10,11-dihydro-8-methylthio-dibenzo[b,f]-thiepin-10-ol; (yellow crystals).

The 2,10-dichloro-10,11-dihydro-8-methylthio-dibenzo[b,f]thiepin is obtained as a crude oil which can be used in the reaction mentioned earlier without further purification.

EXAMPLE 18

Preparation of
3-{2-[4-(10,11-dihydro-3-methyl-8-methylthiodibenzo[b,f]thiepin-10-yl)-1-piperazinyl}-2-oxazolidinone In an analogous manner to that described in Example 16, 3-{2-[4-(10,11-dihydro-3-methyl-8-methylthiodibenzo[b,f,thiepin-10yl)-1-piperazinyl]-ethyl}-2-oxazolidinone (which, after recrystallization from ethanol, melts at 140°–143°C.) is prepared from 10-chloro-10,11-dihydro-3-methyl-8-methylthiodibenzo[b,f]thiepin and 3-[2-(1-piperazinyl)-ethyl]-2-oxazolidinone. The maleate crystallizes from acetone/ether and melts at 151°–153°C.

The 10-chloro-10,11-dihydro-3-methyl-8-methylthio-dibenzo[b,f]thiepin used as the starting material can be prepared in the same manner as described in Example 3 starting from 2-iodo-4-methyl-benzoic acid and 4-methylthio-thiophenol. The following intermediates are obtained in the reaction:

4-methyl-2-[(4'-methylthio-phenyl)thio]-benzoic acid; melting point 250°–255°C.;

4-methyl-2-[(4'-methylthio-phenyl)-thio]-benzyl alcohol; (yellow oil which crystallizes on standing);

4-methyl-2-[4'-methylthio-phenyl)-thio]benzyl chloride; (brown oil);

4-methyl-2-[4'-methylthio-phenyl)-thio]-phenlacetonitrile; (brown oil);

4-methyl-2-[4'-methylthio-phenyl)-thio]-phenylacetic acid; melting point 140°–142°C. after recrystallization from acetone/petroleum ether (low boiling);

3-methyl-8-methylthio-dibenzo[b,f]thiepin-10(11H)-one; melting point 108°–114°C. after recrystallization from ethanol;

10,11-dihydro-3-methyl-8-methylthio-dibenzo[b,f]-thiepin-10-ol (red-brown oil).

The 10-chloro-10,11-dihydro-3-methyl-8-methylthio-dibenzo[b,f]thiepin is obtained as a yellow crystalline mass which can be used in the reaction mentioned earlier without further purification.

EXAMPLE 19

Preparation of
3-{2-[4-(10,11-dihydro-2-methyl-8methylthiodibenzo[b,f]thiepin-10-yl)-1-piperazinyl]-ethyl}-2-oxazolidinone In an analogous manner to that described in Example 16, 3-{2-[4-(10,11-dihydro-2-methyl-8-methylthiodibenzo[b,f]thiepin-10-yl)-1-piperazinyl]-ethyl}-2-oxazolidinone (which, after recrystallization fron ethyl acetate/petroleum ether [low boiling], melts at 122°–123°C.) is prepared from 10-chloro-10,11-dihydro-2-methyl-8-methylthio-dibenzo[b,f]thiepin and 3-[2-(1-piperazinyl)-ethyl]-2-oxazolidinone. The maleate crystallizes from acetone/ether and melts at 156°–158°C. The dimenthanesulfonate crystallizes from methanol/ether and melts at 211°–213°C. (the compound contains 1.54 percent water).

The 10-chloro-10,11-dihydro-2-methyl-8-methylthio-dibenzo[b,f]thiepin used as the starting material can be prepared in the same manner as described in Example 3 starting from 2-iodo-5-methyl-benzoic acid and 4-methylthio-thiophenol. The following intermediates are obtained in the reaction:

5-methyl-2-[(4'-methylthio-phenyl)-thio]-benzoic acid; melting point 153°–157°C.

5-methyl-2-[(4'-methylthio-phenyl)-thio]alcohol; (yellow oil which crystallizes on standing);

5-methyl-2-[(4'-methylthio-phenyl)-thio]benzyl chloride; (brown oil);

5-methyl-2-[(4'-methylthio-phenyl)-thio]-phenylacetonitrile; (red oil);

5-methyl-2-[(4'-methylthio-phenyl)-thio]-phenylacetic acid, melting point 89°–92°C. after recrystallization from ethyl acetate/petroleum ether (low boiling);

2-methyl-8-methylthio-dibenzo[b,f,]thiepin-10(11H)-one, melting point 109°–111°C. after recrystallization from ethanol;

10,11-dihydro-2-methyl-8-methylthio-dibenzo[b,f]-thiepin-10-ol, (red oil).

The 10-chloro-10,11-dihydro-2-methyl-8-methylthio-dibenzo[b,f]thiepin is obtained as a crude, crystalline mass which can be used in the reaction mentioned earlier without further purification.

EXAMPLE 20

Preparation of
3{2-[4-(3-chloro-8-fluoro-10,11-dihydro-dibenzo[b,f]thiepin-10-yl)-1-piperazinyl]-ethyl}-2-oxazolidinone 25 g. of 1-[3-chloro-8-fluoro-10,11-dihydro-dibenzo[b,f]thiepin-10-yl]-piperazine are heated together with 20 g. of pulverized potassium carbonate, 0.4 g. of potassium iodide and 25.6 g. of N-(β-chloro-ethyl)oxazolidinone under reflux conditions over a period of 25 hours. The reaction mixture is poured onto water and equilibrated with benzene. The organic phase is washed with aqueous saturated sodium bicarbonate solution, dried over sodium sulfate and evaporated under reduced pressure. One obtains 3-{2-[4-(3-chloro-8-fluoro-10,11-dihydrodibenzo[b,f]thiepin-10-yl)-1-piperazinyl]-ethyl}-2-oxazolidinone whic is treated with maleic acid to yield the corresponding maleate which after recrystallization from ethanol and ether melts at 143.5°–146°C.

The starting material 1-[3-chloro-8-fluoro-10,11-dihydrodibenzo[b,f]thiepin-10yl]-piperazine utilized above can be prepared from 4-chloro-2-iodo-benzoic acid and 4-fluoro-(thiophenol) in a similar manner to that described in Example 5. The following intermediates are obtained:

4-chloro-6-[4'-fluoro-phenyl)-thio]benzoic acid, melting point 212°–214°;

4-chloro-6-[4'-fluoro-phenyl)-thio]benzyl alcohol, melting point 86°–87°;

4-chloro-6-[4'-fluoro-phenyl)-thio]-benzyl chloride (brown oil);

4-chloro-6-[(4'-fluoro-phenyl)-thio]-phenyl acetonitrile (dark brown oil);

4-chloro-6-[(4'-fluoro-phenyl)-thio]-phenyl acetic acid, melting point after recrystallization from benzene/hexane 96°–100°;

3-chloro-8-fluoro-dibenzo[b,f]thiepin-10(11H)-one, melting point 160°–161°;

3-chloro-8-fluoro-10,11-dihydro-dibenzo[b,f]thiepin-10-ol, melting point 115°–117°;

3,10-dichloro-8-fluoro-10,11-dihydro-dibenzo[b,f]-thiepin, melting point 133.5°–135°.

38.8 G. of 3,10-dichloro-10,11-dihydro-8-fluoro-dibenzo[b,f]thiepin into 100 ml. of chlorofrom are heated with 82 g. of 1-carbethoxypiperazine for 24 hours under reflux conditions. The reaction mixture is poured on ice water and equilibrated with chloroform. The organic phase is dried over magnesium sulfate and evaporated under reduced pressure. Raw 1-carbethoxy-4-(3-chloro-10,11-dihydro-8-fluoro-dibenzo[b,f]thiepin10-yl)-piperazine is obtained as a yellow oil.

63 G. of 1-carbethoxy-4-(3-chloro-10,11-dihydro-8-fluorodibenzo[b,f]thiepin-10-yl)-piperazine, 600 ml. of ethyleneglycol, 2.7 ml. of water and 25 g. of potassium hydroxide are kept for 3 hours at an internal temperature of 160°.

The reaction mixture is diluted with water and extracted with chloroform. The organic phase is treated with aqueous methanesulfonic acid. The aqueous solution is made alkaline with 6N aqueous sodium hydroxide solution and extracted with chloroform. The organic phase is dried over sodium sulfate and evaporaed under reduced pressure. 1-(3-chloro-8-fluoro-10,11-dihydro-dibenzo[b,f]thiepin-10-yl)-piperazine is obtained, which can be used directly in the above reaction.

EXAMPLE 21

Preparation of 3-{2-[4-(8-fluoro-10,11-dihydro-3-methoxy-dibenzo[b,f]thiepin-10-yl)-1-piperazinyl]-ethyl}-2-oxazolidinone 15.4 g. of 10-chloro-8-fluoro-10,11-dihydro-3-methoxy-dibenzo[b,f]thiepin are treated with 41 g. of 3-[2-(1-piperazinyl)ethyl]-2-oxazolidinone and stirred at 120°–130°C. (internal temperature) for 10 minutes. The cooled mixture is treated with 2N sodium hydroxide and extracted with chloroform. The chloroform solution is washed to neutrality with water and shaken out with dilute methanesulfonic acid. The acid solution is made alkaline with sodium hydroxide and the base extracted with chloroform. The organic solution is washed with water, dried over magnesium sulfate and concentrated. The residue is recrystallized from acetone, whereby there is obtained 3-{2-[4-(8-fluoro-10,11-dihydro-3-methoxy-dibenzo[b,f]thiepin-10-yl)-1-piperazinyl]-ethyl}-2-oxazolidinone of melting point 177°–179°C. The corresponding maleate melts at 212°–214°C.

The 10-chloro-8-fluoro-10,11-dihydro-3-methoxy-dibenzo[b,f]thiepin used as the starting material can be prepared in an analogous manner to that described in Example 3. The following intermediates are obtained in the reaction:

4-methoxy-2-[(4'-fluoro-phenyl)-thio]-benzoic acid, melting point 200°–202°C.;

4-methoxy-2-[(4'-fluoro-phenyl)-thio]-benzyl alcohol (yellow oil);

4-methoxy-2-[(4'-fluoro-phenyl)-thio]-benzyl chloride (brown oil);

4-methoxy-2-[(4'-fluoro-phenyl)-thio]-phenylacetonitrile (brown oil);

4-methoxy-2-[(4'-fluoro-phenyl)-thio]-phenylacetic acid, melting point 78°–81°C.;

8-fluoro-3-methoxy-dibenzo[b,f]thiepin-10(11H)-one, melting point 112°–114°C.;

8-fluoro-10,11-dihydro-3-methoxy-dibenzo[b,f]thiepin-10-ol (yellow oil).

The 10-chloro-8-fluoro-10,11-dihydro-3-methoxy-dibenzo[b,f]thiepin obtained melts at 74°–76°C.

EXAMPLE 22

Preparation of 3-{2-[4-(3-chloro-7-fluoro-10,11-dihydro-dibenzo[b,f]thiepin-10-yl)-1-piperazinyl]-ethyl}-2-oxazolidinone 17 G. of 3,10-dichloro-7-fluoro-10,11-dihydro-dibenzo[b,f]thiepin are treated with 45.5 g. of 3-[2-(1-piperazinyl)-ethyl]-2-oxazolidinone and stirred at 120°–130°C. (internal temperature) for 8 minutes. The mixture is treated with 2N sodium hydroxide and extracted with ether. The ether solution is washed to neutrality and shaken out with dilute methanesulfonic acid. The acid solution is made alkaline with sodium hydroxide and extracted with methylene chloride. The organic solution is washed with water and dried over magnesium sulfate. The residue is recrystallized from acetone, whereby there is obtained 3-{2-[4-(3-chloro-7-fluoro-10,11-dihydro-dibenzo[b,f]thiepin-10-yl)-1-piperazinyl]-ethyl}-2-oxazolidinone (melting point 168°–170°C.) which is converted into the dimethanesulfonate (melting point 191°–193°C.) by reaction with methanesulfonic acid.

The 3,10-dichloro-7-fluoro-10,11-dihydro-dibenzo[b,f]thiepin used as the starting material can be prepared in an analogous manner to that described in Example 3 starting from 4-chloro-2-iodo-benzoic acid and 3-fluoro-thiophenol. The following intermediates are obtained in the reaction:

4-chloro-2-[(3'-fluoro-phenyl)-thio]benzoic acid, melting point 183°–185°C.;

4-chloro-2-[(3'-fluoro-phenyl)-thio]-benzyl alcohol (oil);

4-chloro-2-[(3'-fluoro-phenyl)-thio]-benzyl chloride (oil);

4-chloro-2-[(3'-fluoro-phenyl)-thio]-phenylacetonitrile (oil);

4-chloro-2-[(3'-fluorophenyl)-thio]-phenylacetic acid, melting point 117°–119°C.;

3-chloro-7-fluoro-dibenzo[b,f]thiepin-10(11H)-one, melting point 145°–148°C.;

3-chloro-7-fluoro-10,11-dihydro-dibenzo[b,f]thiepin-10-ol, melting point 103°–105°C.

The 3,10-dichloro-7-fluoro-10,11-dihydro-dibenzo[b,f]thiepin obtained melts at 117°–118°C.

EXAMPLE 23

Preparation of
3-{2-[4-(8-fluoro-10,11-dihydro-3-trifluoromethyl-dibenzo[b,f]thiepin-10-yl)-1-piperazinyl]-ethyl}-2-oxazolidinone 11.6 G. of 10-chloro-8-fluoro-10,11-dihydro-3-trifluoromethyl-dibenzo[b,f]thiepin are treated with 27.8 g. of 3-[2-(1-piperazinyl)-ethyl]-2-oxazolidinone and stirred at 115°–120°C. for 10 minutes. The mixture is cooled and treated with 2N sodium hydroxide. The product separating as an oil is extracted with ether. The organic solution is washed to neutrality with water and shaken out with a dilute, aqueous methanesulfonic acid solution. The aqeuous solution is made alkaline with sodium hydroxide and extracted with ether. The ether solution is washed with water, dried over magnesium sulfate and concentrated, whereby there is obtained 3-{2-[4-(8-fluoro-10,11-dihydro-3-trifluoromethyl-dibenzo[b,f]thiepin-10-yl)-1-piperazinyl]-ethyl}-2-oxazolidinone as a yellow oil which is converted into the dimethanesulfonate (melting point 149°–151°C.) by the addition of methanesulfonic acid.

The 10-chloro-8-fluoro-10,11-dihydro-3-trifluoromethyl-dibenzo[b,f]thiepin used as the starting material can be prepared in the same manner as described in Example 3 starting from 2-iodo-4-trifluoromethyl-benzoic acid and 4-fluoro-thiophenol. The following intermediates are obtained in the reaction:

2-[(4'-fluoro-phenyl)-thio]-4-trifluoromethyl-benzoic acid, melting point 161°–163°C.;
2-[(4'-fluorophenyl)-thio]-4-trifluoromethyl-benzyl alcohol, boiling point 0.1 mmHg: 108°–125°C., melting point 53.5°–55°C.;
2-[(4'-fluorophenyl)-thio]-4-trifluoromethyl-benzyl chloride (oil);
2-[(4'-fluoro-phenyl)-thio]-4-trifluoromethyl-phenylacetonitrile, boiling point 0.3 mmHg: 114°–120°C.;
2-[(4'-fluoro-phenyl)-thio]-4-trifluoromethyl-phenylacetic acid, melting point 117°–119°C.;
8-fluoro-3-trifluoromethyl-dibenzo[b,f]thiepin-10(11H)-one, melting point 88°–89°C.;
8-fluoro-10,11-dihydro-3-trifluoromethyl-dibenzo[b,f]thiepin-10-ol (yellow oil).

The 10-chloro-8-fluoro-10,11-dihydro-3-trifluoromethyl-dibenzo[b,f]thiepin obtained melts at 73°–75°C.

EXAMPLE 24

Preparation of
3-{2-[4-(2-chloro-10,11-dihydro-7-methyl-dibenzo[b,f]thiepin-10-yl)-1-piperazinyl]-ethyl}-2-oxazolidinone 20 G. of 2,10-dichloro-10,11-dihydro-7-methyl-dibenzo[b,f]thiepin are stirred with 41 g. of 3-[2-(1-piperazinyl)-ethyl]-2-oxazolidinone and 400 ml. of chloroform at the boiling temperature for 20 hours. The solution is cooled and washed successively with 2N sodium hydroxide and with water. The organic phase is decanted and extracted with dilute methanesulfonic acid. The acid solution is made alkaline with sodium hydroxide and the oil which separates out is shaken out with ether. The ether solution is washed with water, dried over magnesium sulfate and evaporated under reduced pressure, whereby there is obtained 3-{2-[4-(2-chloro-10,11-dihydro-7-methyl-dibenzo[b,f]-thiepin-10-yl)-1-piperazinyl]-ethyl}-2-oxazolidinone (melting point 161°–163°C.) which is converted into the corresponding dimethanesulfonate (melting point 187°–189°C.) by reaction with methanesulfonic acid.

The 2,10-dichloro-10,11-dihydro-7-methyl-dibenzo[b,f]-thiepin used as the starting material can be prepared in an analogous manner to that described in Example 3 starting from 5-chloro-2-iodo-benzoic acid and 3-methyl-thiophenol. The following intermediates are obtained in the reaction:

3-chloro-6-[(3'-methyl-phenyl)-thio]-benzoic acid, melting point 163°–166°C.;
3-chloro-6-[(3'-methyl-phenyl)-thio]-benzyl chloride (brown oil);
3-chloro-6-[(3'-methyl-phenyl)-thio]-phenylacetonitrile (brown oil);
3-chloro-6-[(3'-methyl-phenyl)-thio]-phenylacetic acid, melting point 112°–114°C;
2-chloro-7-methyl-dibenzo[b,f]thiepin-10(11H)-one, melting point 113°–115°C.;
2-chloro-10,11-dihydro-7-methyl-dibenzo[b,f]thiepin-10-ol, melting point 136°–138°C..

The 2,10-dichloro-10,11-dihydro-7-methyl-dibenzo[b,f]-thiepin obtained melts at 145°–147°C.

The following Examples illustrate pharmaceutical preparations containing the dibenzo[b,f]thiepins provided by the present invention:

Example A
TABLETS

| | Per Tablet |
|---|---|
| 3-{2-[4-(8-fluoro-10,11-dihydro-2-methyl-dibenzo[b,f]thiepin-10-yl)-1-piperazinyl]-ethyl}-2-oxazolidinone | 100 mg. |
| Lactose | 202 mg. |
| Maize Starch | 80 mg. |
| Hydrolyzed Maize Starch | 20 mg. |
| Calcium Stearate | 8 mg. |
| Total Weight | 410 mg. |

The active ingredient, lactose, maize starch and hydrolyzed maize starch are mixed together and granulated with water to a viscous paste. This paste is passed through a sieve and subsequently dried overnight at 45°C. The dried granulate is passed through a sieve and subsequently mixed with the calcium stearate. The mixture obtained is pressed into tablets of weight 410 mg. and about 10 mm. diameter.

Example B
TABLETS

| | Per Tablet |
|---|---|
| 3-{2-[4-(8-fluoro-10,11-dihydro-2-methyl-dibenzo[b,f]thiepin-10-yl)-1-piperazinyl]-ethyl}-2-oxazolidinone | 25.0 mg. |
| Lactose | 114.0 mg. |
| Maize Starch | 50.0 mg. |
| Gelatinized Maize Starch | 8.0 mg. |
| Calcium Stearate | 3.0 mg. |
| Total Weight | 200.0 mg |

The active ingredient, lactose, maize starch and gelatinized maize starch are mixed intimately with one another. The mixture is passed through a comminuting machine and subsequently moistened with water to give a thick paste. The moist mass is passed through a sieve, and thereafter, is dried at 45°C. The dried granulate is mixed thoroughly with the calcium stearate and this mass is pressed into tablets of weight 200 mg. and about 8 mm. diameter.

Example C
TABLETS

| | Per Tablet |
|---|---|
| 3-{2-[4-(8-fluoro-10,11-dihydro-2-methyl-dibenzo[b,f]thiepin-10-yl)-1-piperazinyl]-ethyl}-2-oxazolidinone dimethane-sulfonate | 14.5 mg. |
| Lactose | 124.5 mg. |
| Maize Starch | 50.0 mg. |
| Gelatinized Maize Starch | 8.0 mg. |
| Calcium Stearate | 3.0 mg. |
| Total Weight | 200.0 mg. |

The active ingredient, lactose, maize starch and gelatinized maize starch are mixed intimately with one another. The mixture is passed through a comminuting machine and subsequently moistened with water to give a thick paste. The moist mass is passed through a sieve, and thereafter, is dried at 45°C. The dried granulate is mixed throughly with the calcium stearate, and this mass is pressed into tablets of weight 200 mg. and about 8 mm. diameter.

Example D
TABLETS

| | Per Tablet |
|---|---|
| 1-{2-[4-(8-chloro-10,11-dihydro-2-methyl-dibenzo[b,f]thiepin-10-yl)-1-piperazinyl]-ethyl}-2-pyrrolidinone maleate | 25.00 g. |
| Lactose | 110 g. |
| Maize Starch | 61.00 g. |
| Talc | 3.40 g. |
| Magnesium Stearate | 0.60 g. |
| Total Weight | 200.00 g. |

The ingredients are mixed intimately with one another and pressed into tablets each of 200 mg. Subsequently, they are coated with ethyl cellulose and Carbowax.

Example E
CAPSULES

| | Per Capsule |
|---|---|
| 3-{2-[4-(8-fluoro-10,11-dihydro-2-methyl-dibenzo[b,f]thiepin-10-yl)-1-piperazinyl]-ethyl}-2-oxazolidinone dimethanesulfonate | 29.0 mg. |
| Lactose | 156.0 mg. |
| Maize Starch | 30.0 mg. |
| Talc | 5.0 mg. |
| Total Weight | 220.0 mg. |

The active ingredient, lactose and maize starch are mixed intimately with one another and passed through a comminuting machine. Then, the mixture is mixed thoroughly with the talc and filled into hard gelatin capsules.

Example F
CAPSULES

| | Per Capsule |
|---|---|
| 3-{2-[4-(8-fluoro-10,11-dihydro-2-methyl-dibenzo[b,f]-thiepin-10-yl)-1-piperazinyl]-ethyl}-2-oxazolidinone | 25.5 mg. |
| Lactose | 159.5 mg. |
| Maize Starch | 30.0 mg. |
| Talc | 5.0 mg. |
| Total Weight | 220.0 mg. |

The active ingredient, lactose and maize starch are mixed intimately with one another and passed through a comminuting machine. Then, the mixture is mixed thoroughly with the talc and filled into hard gelatin capsules.

Example G
PARENTERAL PREPARATION

Each 1 ml. ampule contains:

| | |
|---|---|
| 3-{2-[4-(8-fluoro-10,11-dihydro-2-methyl-dibenzo[b,f]thiepin-10-yl)-1-piperazinyl]-ethyl}-2-oxazolidinone | 10.20 mg. (2 percent excess) |
| Methanesulfonic acid for injection | 2.22 mg. |
| Glucose for injection | 40.0 mg. |
| Water for injection q.s. ad | 1 ml. |

In a glass vessel, there are dissolved in 8000 ml. of water for injection with stirring at room temperature, successively:

22.2 g. of methanesulfonic acid for injection,
102 g. of active ingredient and
400 g. of glucose.

Subsequently, water for injection is added to a total volume of 10,000 ml. The solution is either aseptically filtered, filled into colorless ampules, gassed with nitrogen and sealed or filled into colorless ampules, gassed with nitrogen, sealed and subsequently sterilized in a current of steam or autoclaved at 120°C. for 30 minutes.

Instead of the active ingredients used in Examples A–G there can also be used in the preparations described therein, other dibenzo[b,f]thiepins of formulas I and Ia of the invention, for example:

3-{2-[4-(2-chloro-7-fluoro-10,11-dihydro-dibenzo[b,f]thiepin-10-yl)-1-piperazinyl]-ethyl}-2-oxazolidinone or the maleate thereof;

3-{2-[4-(2-chloro-8-fluoro-10,11-dihydro-dibenzo[b,f]-thiepin-10-yl)-1-piperazinyl]-ethyl}-2-oxazolidinone or the maleate thereof;

3-{2-[4-(10,11-dihydro-2-methyl-8-methylthio-dibenzo[b,f]thiepin-10-yl)-1-piperazinyl]-ethyl}-2-oxazolidinone or the maleate thereof.

Exemplary end products encompassed by claim 1 are e.g., the following:

1-{2-[4-(8-chloro-10,11-dihydro-3-methoxy-dibenzo[b,f]thiepin-10-yl)-1-piperazinyl]-ethyl}-2-pyrrolidinone;

1-{2-[4-(8-chloro-10,11-dihydro-3-methyl-dibenzo[b,f]thiepin-10-yl)-1-piperazinyl]-ethyl}-2-pyrrolidinone;

1-{2-[4-(8-fluoro-10,11-dihydro-3-methoxy-dibenzo[b,f]thiepin-10-yl)-1-piperazinyl]-ethyl}-2-pyrrolidinone;

1-{2-[4-(8-fluoro-10,11-dihydro-3-trifluoromethyl-dibenzo[b,f]thiepin-10-yl)-1-piperazinyl]-ethyl}-2-pyrrolidinone;

1-{2-[4-(8-dimethylsulfamoyl-10,11-dihydro-3-methoxy-dibenzo[b,f]thiepin-10-yl)-1-piperazinyl]-ethyl}-2-pyrrolidinone;

1-{2-[4-(2-chloro-10,11-dihydro-8-methylthio-b,f]thiepin-10-yl)-1-piperazinyl]-ethyl}-2-pyrrolidinone;

1-{2-[4-(8-methyl-10,11-dihydro-3-trifluoromethyl-dibenzo[b,f]thiepin-10-yl)-1-piperazinyl]-ethyl}-2-pyrrolidinone;

and their pharmaceutically acceptable acid addition salts;

the compounds corresponding to the aforegoing which are 2-imidazolidinones, 3-methyl-2-imidazolidinones, 2-benzimidazolidinones, 2-piperidones, 2-oxazolidinones or 2-thiazolidinones instead of 2-pyrrolidinones.

We claim:
1. A compound of the formula

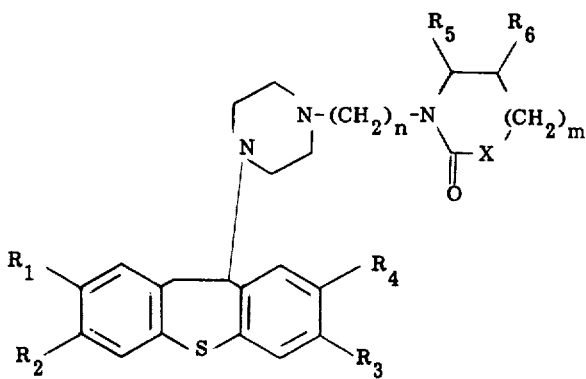

wherein one of $R_1$ and $R_2$ is hydrogen and the other is methyl, methoxy, methylthio, dimethylsulfamoyl, chloro, fluoro or trifluoromethyl; one of $R_3$ and $R_4$ is hydrogen and the other is methyl, methoxy, methylthio, dimethylsulfamoyl, chloro, fluoro or trifluoromethyl; $n$ is 2 or 3; $m$ is 0; X is oxygen, and $R_5$ and $R_6$ are hydrogen or taken together are the group

or a salt thereof with a pharmaceutically acceptable acid.

2. A compound in accordance with claim 1, wherein $R_2$ and $R_3$ are hydrogen; $R_1$ is methyl and $R_4$ is chloro.

3. A compound in accordance with claim 1, wherein $R_2$ and $R_4$ are hydrogen; $R_1$ is chloro and $R_3$ is fluoro.

4. A compound in accordance with claim 1, wherein $R_1$ and $R_3$ are hydrogen; $R_2$ is methoxy and $R_4$ is methylthio.

5. A compound in accordance with claim 1, wherein $n$ is 2; and $R_5$ and $R_6$ are hydrogen.

6. A compound in accordance with claim 2, wherein $n$ is 2; and $R_5$ and $R_6$ are hydrogen.

7. A compound in accordance with claim 3, wherein $n$ is 2; and $R_5$ and $R_6$ are hydrogen.

8. A compound in accordance with claim 4, wherein $n$ is 2; and $R_5$ and $R_6$ are hydrogen.

9. A compound in accordance with claim 1, wherein $R_2$ and $R_3$ are hydrogen, $R_1$ is methyl and $R_4$ is fluoro.

10. A compound in accordance with claim 1, wherein $R_2$ and $R_3$ are hydrogen, $R_1$ is methyl and $R_4$ is methylthio.

11. A compound in accordance with claim 1, wherein $R_2$ and $R_3$ are hydrogen, $R_1$ is chloro and $R_4$ is fluoro.

12. A compound in accordance with claim 1, 3-{2-[4-(8-fluoro-10,11-dihydro-2-methyl-dibenzo[b,f]thiepin-10-yl)-1-piperazinyl]-ethyl}-2-oxazolidinone.

13. A compound in accordance with claim 1, 3-{2-[4-(2-chloro-8-fluoro-10,11-dihydro-dibenzo[b,f]thiepin-10-yl)-1-piperazinyl]-ethyl}-2-oxazolidinone.

14. A compound in accordance with claim 1, 3-{2-[4-(10,11-dihydro-2-methyl-8-(methylthio)-dibenzo[b,f]thiepin-10-yl)-1-piperazinyl]-ethyl}-2-oxazolidinone.

15. A compound in accordance with claim 1, 3-{2-[4-(2-chloro-7-fluoro-10,11-dihydro-dibenzo[b,f]thiepin-10-yl)-1-piperazinyl]-ethyl}-2-oxazolidinone.

* * * * *